(12) United States Patent
Josel et al.

(10) Patent No.: US 11,125,695 B2
(45) Date of Patent: Sep. 21, 2021

(54) BRANCHED-CHAIN AMINES IN ELECTROCHEMILUMINESCENCE DETECTION

(71) Applicant: Roche Diagnostics Operations, Inc., Indianapolis, IN (US)

(72) Inventors: Hans-Peter Josel, Weilheim (DE); Herbert Andres, Penaberg (DE); Michaela Windfuhr, Iffeldorf (DE); Oliver Larbolette, Penzberg (DE); Stefan Quint, Munich (DE)

(*) Notice: Subject to any disclaimer, the term of this patent is extended or adjusted under 35 U.S.C. 154(b) by 469 days.

(21) Appl. No.: 16/111,646

(22) Filed: Aug. 24, 2018

(65) Prior Publication Data

US 2018/0364175 A1 Dec. 20, 2018

Related U.S. Application Data

(63) Continuation of application No. PCT/EP2017/055671, filed on Mar. 10, 2017.

(30) Foreign Application Priority Data

Mar. 11, 2016 (EP) .................... 16159835

(51) Int. Cl.
| | | |
|---|---|---|
| G01N 21/76 | (2006.01) | |
| G01N 21/66 | (2006.01) | |
| G01N 33/543 | (2006.01) | |
| C07F 15/00 | (2006.01) | |
| G01N 27/30 | (2006.01) | |

(52) U.S. Cl.
CPC ......... *G01N 21/76* (2013.01); *C07F 15/0033* (2013.01); *C07F 15/0046* (2013.01); *G01N 21/66* (2013.01); *G01N 33/5438* (2013.01); *G01N 27/308* (2013.01); *G01N 2458/30* (2013.01)

(58) Field of Classification Search
CPC .... G01N 21/76; G01N 21/66; G01N 33/5438; G01N 2458/30; C07F 15/0046; C07F 15/0033
See application file for complete search history.

(56) References Cited

U.S. PATENT DOCUMENTS

| | | |
|---|---|---|
| 4,554,088 A | 11/1985 | Whitehead et al. |
| 4,628,037 A | 12/1986 | Chagnon et al. |

(Continued)

FOREIGN PATENT DOCUMENTS

| | | |
|---|---|---|
| EP | 0441875 B1 | 7/1997 |
| EP | 0720614 B1 | 5/2000 |

(Continued)

OTHER PUBLICATIONS

International Search Report dated May 5, 2017, in Application No. PCT/EP2017/055671, 3 pp.

(Continued)

*Primary Examiner* — Brian J. Sines

(57) ABSTRACT

The disclosure concerns methods for the detection of an analyte in a sample by electrochemiluminescence using new reagent compositions. New reagent compositions, reagent kits for measuring electrochemiluminscence (ECL) and electrochemiluminescence detection methods using the new reagent compositions are disclosed. In particular, the disclosure relates to the use of novel combinations of compounds which can be used in said measurements to provide improved assay performance.

15 Claims, 7 Drawing Sheets

(56) References Cited

U.S. PATENT DOCUMENTS

| | | |
|---|---|---|
| 4,695,393 A | 9/1987 | Whithead et al. |
| 4,698,302 A | 10/1987 | Whitehead et al. |
| 4,965,392 A | 10/1990 | Fritzberg et al. |
| 5,093,268 A | 3/1992 | Leventis et al. |
| 5,147,806 A | 9/1992 | Kamin et al. |
| 5,202,238 A | 4/1993 | Fell, Jr. et al. |
| 5,204,244 A | 4/1993 | Fell et al. |
| 5,240,863 A | 8/1993 | Shibue et al. |
| 5,308,754 A | 5/1994 | Kankare et al. |
| 5,324,457 A | 6/1994 | Zhang et al. |
| 5,543,112 A | 8/1996 | Ghead et al. |
| 5,591,581 A | 1/1997 | Massey et al. |
| 5,597,910 A | 1/1997 | Gudibande et al. |
| 5,641,623 A | 6/1997 | Martin |
| 5,643,713 A | 7/1997 | Liang et al. |
| 5,679,519 A | 10/1997 | Oprandy |
| 5,705,402 A | 1/1998 | Leland et al. |
| 5,731,147 A | 3/1998 | Bard et al. |
| 5,786,141 A | 7/1998 | Bard et al. |
| 5,846,485 A | 12/1998 | Leland et al. |
| 5,866,434 A | 2/1999 | Massey et al. |
| 5,935,779 A | 8/1999 | Massey et al. |
| 6,066,448 A | 5/2000 | Wohlstadter et al. |
| 6,136,268 A | 10/2000 | Ala-Kleme et al. |
| 6,207,369 B1 | 3/2001 | Wohlstadter et al. |
| 6,316,607 B1 | 11/2001 | Massey et al. |
| 6,451,225 B1 | 9/2002 | Leland et al. |
| 2007/0034529 A1 | 2/2007 | Bard et al. |

FOREIGN PATENT DOCUMENTS

| | | |
|---|---|---|
| EP | 1051621 A1 | 11/2000 |
| EP | 1892524 A1 | 2/2008 |
| WO | 1987/006706 A1 | 11/1987 |
| WO | 1990/005296 A1 | 5/1990 |
| WO | 1992/014139 A1 | 8/1992 |
| WO | 1997/036931 A1 | 10/1997 |
| WO | 1998/012539 A1 | 3/1998 |
| WO | 1998/057154 A1 | 12/1998 |
| WO | 1999/014599 A1 | 3/1999 |
| WO | 1999/032662 A1 | 7/1999 |
| WO | 1999/058962 A1 | 11/1999 |
| WO | 1999/063347 A2 | 12/1999 |
| WO | 2000/003233 A1 | 1/2000 |
| WO | 2003/002974 A2 | 1/2003 |
| WO | 2004/001380 A2 | 12/2003 |
| WO | 2007/002580 A2 | 1/2007 |
| WO | 2012/055815 A1 | 5/2012 |
| WO | 2012/107419 A1 | 8/2012 |
| WO | 2012/107420 A1 | 8/2012 |
| WO | 2014/019707 A2 | 2/2014 |
| WO | 2014/019708 A1 | 2/2014 |
| WO | 2014/019709 A2 | 2/2014 |
| WO | 2014/019710 A1 | 2/2014 |
| WO | 2014/019711 A1 | 2/2014 |

OTHER PUBLICATIONS

Knight, Andrew W. and Greenway, Gillian M., Relationship Between Structural Attributes and Observed Electrogenerated Chemiluminescence (ECL) Activity of Tertiary Amines as Potential Analytes for the Tris(2,2-Bipyridine)Ruthenium(ii) ECL Reaction A Review, The Analyst, 1996, pp. 101R-106R, vol. '121.

Butler, John E., Sold Supports in Enzyme-Linked Immunosorbent Assay and Other Solid-Phase Immunoassays, Methods, 2000, pp. 4-23, vol. 22.

Gheorghe, Ruxandra et al., Enantiomerically Pure Quaternary Ammonium Salts with a Chiral Alkyl Chain N(CH3)(n-C3H7)2(sec-C4H9)I: Synthesis and Physical Studies, Chirality, 2008, pp. 1085-1091, vol. 20.

Lonberg, Nils, Human antibodies from transgenic animals, Nature Biotechnology, 2005, pp. 1117-1125, vol. 23.

Martin, Charles R. and Mitchell, David T., Nanomaterials in Analytical Chemistry, Analytical Chemistry News & Features, 1998, pp. 332A-327A.

Miao, Wujian et al., Electrogenerated Chemiluminescence 69: The Tris(2,2'-bipyridine)ruthenium(II), (Ru(bpy)32+)/Tri-n-propylamine (TPrA) System Revisted—A New Route Involving TPrA•+ Cation Radicals, Journal of the American Chemical Society, 2002, pp. 14478-14485, vol. 124.

Morrison, Sherie L. et al., Chimeric human antibody molecules: Mouse antigen-binding domains with human constant region domains, Proceedings of the National Academy of Sciences USA, 1984, pp. 6851-6855, vol. 81.

Neuberger, M.S. et al., A hapten-specific chimaeric IgE antibody with human physiological effector function, Nature, 1985, pp. 268-270, vol. 314.

Richter, Mark M., Electrochemiluminescence (ECL), Chemical Reviews, 2004, pp. 3003-3036, vol. 104.

Riechmann, Lutz et al., Reshaping human antibodies for therapy, Nature, 1988, pp. 323-327, vol. 332.

Takayama, Chiyozo et al., Quantitative Separation of Electronic and Steric Substituent Effects in Reactions between Aliphatic Amines and Electron Acceptors, Journal of Organic Chemistry, 1979, pp. 2871-2879, vol. 44, No. 16.

Tijssen, P., Practice and Theory of Enzyme Immunoassays, 1990, pp. 43-78, 108-115, Elsevier.

BRANCHED-CHAIN AMINES IN ELECTROCHEMILUMINESCENCE DETECTION

CROSS-REFERENCE TO RELATED APPLICATIONS

This application is a continuation of International Application No. PCT/EP2017/055671 filed Mar. 10, 2017, which claims priority to European Application No. 16159835.4 filed Mar. 11, 2016, the disclosures of which are hereby incorporated by reference in their entirety.

FIELD OF THE INVENTION

The invention concerns methods for the detection of an analyte in a sample by electrochemiluminescence using new reagent compositions. New reagent compositions, reagent kits for measuring electrochemiluminscence (ECL) and electrochemiluminescence detection methods using the new reagent compositions are disclosed. In particular, the invention relates to the use of novel combinations of compounds which can be used in said measurements to provide improved assay performance.

BACKGROUND

Methods for measuring electrochemiluminescent phenomena have been known for some years. Such methods make use of the ability of special metal complexes to achieve, by means of oxidation and reduction reactions, an excited state from which they decay to ground state, emitting photons. For review see Richter, M. M., Chem. Rev. 104 (2004) 3003-3036.

At this time, there are a number of commercially available instruments that utilize electrochemiluminescence (ECL) for analytical measurements, e.g. in the field of in vitro diagnostic application. Species that can be induced to emit ECL (ECL-active species) have been used as ECL labels. Examples of ECL labels include organometallic compounds such as the tris-bipyridyl-ruthenium (RuBpy) moiety where the metal is from, for example, the metals of group VII and VIII, including Re, Ru, Ir and Os. Species that react with the ECL label in the ECL process are referred to herein as ECL coreactants. Commonly used coreactants for ECL include tertiary amines (e.g. tripropylamine (TPA)), oxalate, and persulfate. The light is generated by ECL labels or ECL ligands; the participation of the binding reagent in a binding interaction can be monitored by measuring ECL emitted from the ECL label. Alternatively, the ECL signal from an ECL-active compound may be indicative of the chemical environment (see, e.g., U.S. Pat. Nos. 5,641,623 and 5,643,713, which describes ECL assays that monitor the presence or destruction of special ECL coreactants). For more background on ECL, ECL labels, ECL assays and instrumentation for conducting ECL assays see U.S. Pat. Nos. 5,093,268; 5,147,806; 5,240,863; 5,308,754; 5,324,457; 5,591,581; 5,597,910; 5,679,519; 5,705,402; 5,731,147; 5,786,141; 5,846,485; 5,866,434; 6,066,448; 6,136,268 and 6,207,369, and EP 0 441 875, and published PCT Nos. WO90/05296, WO97/36931; WO98/12539; WO99/14599; WO99/32662; WO99/58962; WO99/63347; WO00/03233 and WO98/57154.

Commercially available ECL instruments for in vitro diagnostics have demonstrated exceptional performance. They have become widely used for reasons including their excellent sensitivity, dynamic range, precision, and tolerance of complex sample matrices. The commercially available instrumentation uses flow cell-based designs with permanent reusable flow cells.

Available sample volumes for the determination of analytes are often limited and more and more different analytes have to be determined out of one sample. Also the development of faster laboratory equipment for assay automation and more sensitive methods for the detection of analytes are required. This leads to the need for highly sensitive and specific electrochemiluminescent assays and methods for performing them. In addition improvements associated with safety hazards or environmental concerns should be considered.

In particular, still more sensitive detection of analytes would be of great advantage. Thus, the object of the present invention was to improve said known methods and reagent compositions especially with respect to enhancement of the ECL signal and an improved analyte detection in combination with electrochemiluminescent procedures. It would be desirable to find novel signal enhancing reagents and/or compounds with improved performance in electrochemiluminescent assays.

SUMMARY OF THE INVENTION

In an embodiment, the present invention relates to a method of detecting an electrochemiluminescence (ECL) signal comprising
 a) contacting a reaction composition comprising
  i) at least one branched-chain tertiary amine and
  ii) an ECL compound comprising a transition metal complex with an electrode,
 b) electrochemically triggering the release of luminescence, and
 c) detecting the ECL signal.

The present invention, in a further embodiment, concerns a method for detecting an analyte in a sample via electrochemiluminescence detection, comprising the steps of:
 a) incubating the sample with a detection reagent labeled with an electrochemiluminescent group comprising a transition metal complex, in an embodiment comprising a tris(2,2'-bipyridyl)ruthenium complex (Ru(bpy)$_3^{2+}$),
 b) separating analyte-bound and analyte-free labeled detection reagent,
 c) contacting the separated analyte-bound labeled detection reagent with a branched-chain tertiary amine of the present invention and with an electrode,
 d) electrochemically triggering the release of luminescence, and
 e) detecting the electrochemiluminescence (ECL) signal thereby detecting the analyte.

In a further embodiment, the present invention relates to a reagent composition for detecting ECL, comprising
 i) a branched-chain tertiary amine, in particular a branched-chain tertiary amine of Formula I

as coreactant, and
 ii) a further ECL reagent.

In an embodiment, the present invention also relates to an ECL reaction composition comprising i) at least one ECL compound comprising a transition metal complex and ii) at least one branched-chain tertiary amine as a coreactant.

The present invention also relates to a use of a branched-chain tertiary amine as specified in any one of the present invention, of a reagent composition according to the present invention, and/or of reaction composition according to the present invention in the detection of ECL.

Further, the present invention relates to a kit for detecting ECL comprising i) a branched-chain tertiary amine and ii) an ECL reagent.

Moreover, the present invention relates to an ECL device comprising a branched-chain tertiary amine as specified in any one of embodiments of the present invention.

Furthermore, the present invention relates to an ECL device comprising a branched-chain tertiary amine of the present invention.

The invention, as well as additional objects, features and advantages thereof, will be understood more fully from the following detailed description of certain embodiments.

DETAILED DESCRIPTION

Figure 1:
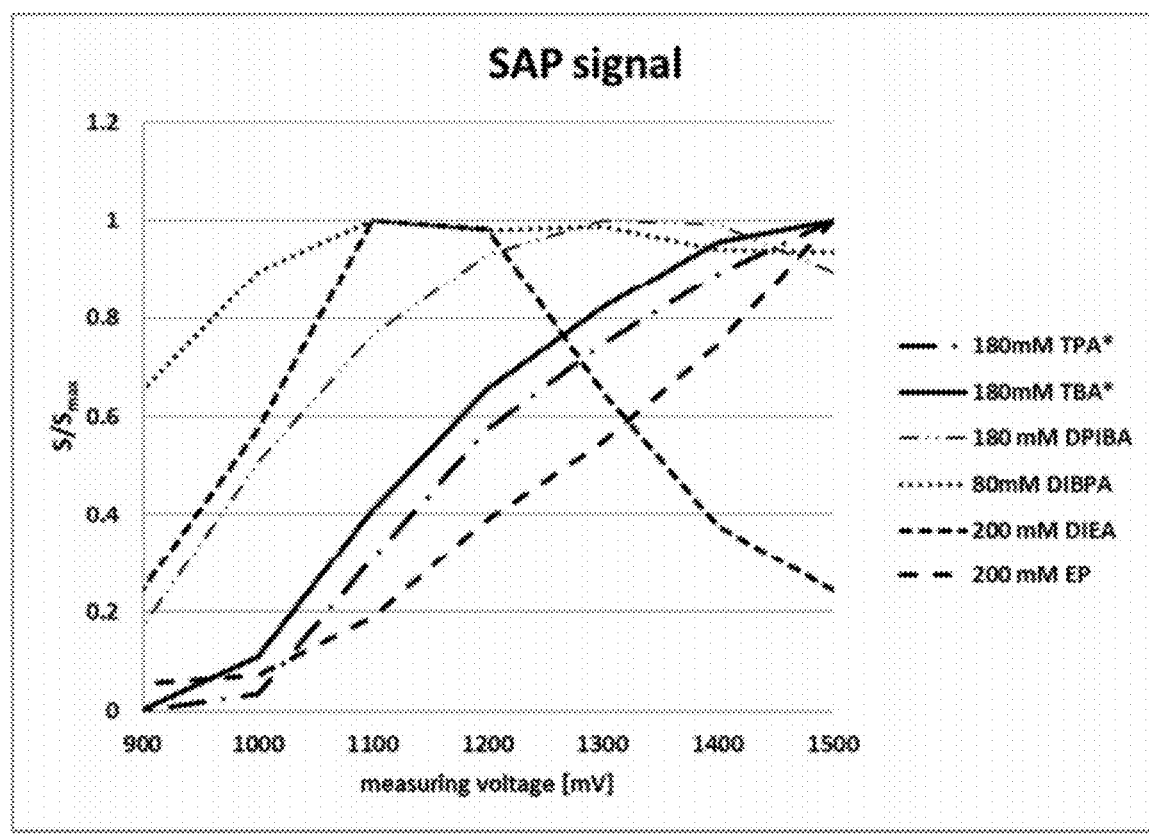
FIG. 1 shows the ECL signal measured in dependence on the applied measuring voltage in an artificial immunoassay including RuBpy labeled microparticles ("SAP assay") for 6 different coreactands. X-Axis: measuring voltage in mV, Y-Axis: signal intensity/maximal signal intensity (S/Smax); TPA: Tripropylamine, TBA: Tributylamine, EP: Ethylpiperidine, DIEA: N,N-Diisopropyl-N-ethylamine, DPIBA: N,N-Dipropyl-N-(sec-butyl)amine, DIBPA: N,N-Di(sec-butyl)-propylamine.

The practicing of the present invention will employ, unless otherwise indicated, conventional techniques of chemistry, molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Unless defined otherwise, technical and scientific terms used herein have the same meaning as commonly understood by one of ordinary skill in the art to which this invention belongs. Singleton et al., Dictionary of Microbiology and Molecular Biology, $2^{nd}$ ed., J. Wiley & Sons, New York (1994); March, Advanced Organic Chemistry Reactions, Mechanisms and Structure, 4th ed., John Wiley & Sons, New York (1992); Lewin, B., Genes V, published by Oxford University Press (1994), ISBN 0-19-854287 9); Kendrew, J. et al. (eds.), The Encyclopedia of Molecular Biology, published by Blackwell Science Ltd. (1994), ISBN 0-632-02182-9); and Meyers, R. A. (ed.), Molecular Biology and Biotechnology: a Comprehensive Desk Reference, published by VCH Publishers, Inc. (1995), ISBN 1-56081-569 8) provide one skilled in the art with a general guidance to many of the terms used in the present application.

All references cited herein, including patent applications and publications, are incorporated by reference in their entirety.

As used herein, each of the following terms has the meaning associated with it in this section.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which a solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding further embodiments of the invention, without any restrictions regarding the scope of the invention and without any restriction regarding the possibility of combining the features introduced in such way with other optional or non-optional features of the invention.

The articles "a" and "an" are used herein to refer to one or to more than one (i.e. to at least one) of the grammatical object of the article. By way of example, "an analyte" means one analyte or more than one analyte. The term "at least" is used to indicate that optionally one or more further objects may be present. By way of example, an array comprising at least two discrete areas may optionally comprise two or more discrete test areas. The expression "one or more", in an embodiment, denotes 1 to 50, in a further embodiment 1 to 20, in a further embodiment 1, 2, 3, 4, 5, 6, 7, 8, 9, 10, 12, or 15. Moreover, if not noted otherwise, the term "about" relates to the indicated value ±20%.

The methods of the present invention, in an embodiment, are in vitro methods. Moreover, they may comprise steps in addition to those explicitly mentioned herein. For example, further steps may relate, e.g., to obtaining a sample for analysis, or calculating a measurement value or a corrected measurement value from an ECL value detected. Moreover, one or more of the steps of the methods of the present invention may be performed by automated equipment.

"Detection" includes any method of detecting, including direct and indirect detection. The term "detection" is used in the broadest sense to include both qualitative and quantitative measurements of an electrochemiluminescence signal; and qualitative and quantitative measurements of an analyte, herein also referred to as measurements of an analyte. In one aspect, a detection method as described herein is used to identify the mere presence of ECL in a detection composition or of an analyte of interest in a sample. In another aspect, the method can be used to quantify an ECL signal in a detection composition or an amount of analyte in a sample. For quantitative detection, either the absolute or precise intensity of an ECL signal or amount of an analyte will be detected; or the relative intensity of an ECL signal or amount of an analyte will be detected. The relative intensity or amount may be detected in a case where the precise intensity or amount can or shall not be detected. In said case, it can be detected whether the intensity or amount is increased or diminished with respect to a second sample providing a reference intensity or comprising said analyte in a second, in an embodiment pre-determined, amount.

In an embodiment, detecting is measuring. The terms "measuring"/"measurement" in science relate to the process of estimating or determining the magnitude of a quantity, such as length or mass, relative to a unit of measurement, such as a meter or a kilogram. Measuring/measurement uses a reference point against which other things can be evaluated. The term measurement can also be used to refer to a specific result (determined values) obtained from a measurement process. It is a basis for comparison. The skilled artisan is aware of materials and methods to correlate measured signals or determined values to concentrations.

To "reduce" or "inhibit" is to decrease or reduce an activity, function, and/or amount as compared to a reference. By reduce or inhibit is meant the ability to cause an overall decrease in an embodiment of 10% or greater, in a further embodiment of 25% or greater, in a further embodiment of 50%, 75%, 90%, 95%, or greater.

To "enhance", e.g. to "enhance specific signals" or "the enhancement of ECL signals", is to increase or rise an activity, function, and/or amount as compared to a reference. By increase or rise is meant the ability to cause an overall increase in an embodiment of 10% or greater, in a further embodiment of 25% or greater, in a further embodiment of 50% or greater.

The term "luminescence" refers to any emission of light that does not derive energy from the temperature of an energy source (for example, a source of electromagnetic radiation, a chemical reaction, mechanical energy). In general, the source causes an electron of an atom to move from a lower energy state into an "excited" higher energy state; then the electron releases that energy in the form of emitted light when it falls back to a lower energy state. Such emission of light usually occurs in the visible or near-visible range of the electromagnetic spectrum. The term "luminescence" includes, but is not limited to, such light emission phenomena such as phosphorescence, fluorescence, bioluminescence, radioluminescence, electroluminescence, electrochemiluminescence and thermo-luminescence. In an embodiment, luminescence is electrochemiluminescence (ECL). As is understood by the skilled person, ECL is luminescence produced during an electrochemical reaction as specified elsewhere herein. Accordingly, an ECL signal, in an embodiment, is a detectable electrochemiluminescent signal, whether visibly detectable or detectable by using suitable instrumentation, in an embodiment photometric instrumentation.

The term "contacting", as used in the context of the methods of the present invention, is understood by the skilled person. In an embodiment, the term relates to bringing a compound into physical contact with a further compound or device, thereby allowing the compound and the further compound or device to interact. In particular the term relates to bringing a branched-chain tertiary amine of the present invention into physical contact with an ECL compound comprising a transition metal complex and an electrode; and/or to bringing a detection reagent into physical contact with a sample.

The term "transition metal complex", as used herein, relates to a compound comprising a transition metal ion complexed by an appropriate complexing agent. The term "compound comprising a transition metal complex" relates to any compound comprising a transition metal complex and a second chemical compound. In an embodiment, the transition metal complex and the second chemical compound are linked covalently. In a further embodiment, the second chemical compound is a biological macromolecule. In further embodiment, the second chemical compound is an analyte specific reagent as specified below. As used herein, the term "ECL compound comprising a transition metal complex" relates to a compound comprising a transition metal complex wherein the transition metal complex emits ECL under appropriate conditions. In an embodiment, the ECL compound is comprising a transition metal complex. In an embodiment, the transition metal is selected from the group consisting of Ruthenium (=Ru), Iridium (=Ir), Rhenium, Osmium, Europium, Terbium, and Dysprosium; in a further embodiment, the transition metal is Ruthenium, Iridium, Rhenium, or Osmium; in a further embodiment, the transition metal is Ruthenium or Iridium. Appropriate complexing agents are known in the art and include bipyridine, phenanthroline, phenyl-pyridine, phenyl-quinoline, phenylphenanthridine or pyridine-2-carboxylic acid.

ECL compounds comprising a transitional metal complex are for example disclosed in WO 8706706 A1, WO 2003002974, EP720614(A1) and U.S. Pat. No. 6,451,225 (B1).

In an embodiment, the ECL compound comprising a transition metal complex is selected from the group consisting of Ru(bpy)2-bpyCO-OSu, which is the N-hydroxy-succinimide ester of CAS Reg. Nr.115239-59-3 (Ru(bpy)2-bpyCO2H)=BPRu, also known in the art as Ruthenium(1+), bis(2,2'-bipyridine-κN1, κN1')(4'-methyl[2,2'-bipyridine]-4-butanoato-κN1,κN1')-, (OC-6-33)-, hydrogen hexafluorophosphate(1-) (1:1:2), also known as Ruthenium(1+), bis(2,2'-bipyridine-N,N')(4'-methyl[2,2'-bipyridine]-4-butanoato-N1,N1')-, (OC-6-33)-, hydrogen hexafluorophosphate(1-) (1:1:2));

Sulfo-BPRu NHS Ester (=CAS Reg. Number 482618-42-8 also known in the art as Ruthenate(2-), bis [[2,2'-bipyridine]-4,4'-dimethanesulfonato(2-)-κN1,κN1'][1-[4-(4'-methyl[2,2'-bipyridin]-4-yl-κN1,κN1')-1-oxobutoxy]-2,5-pyrrolidinedione]-, sodium (1:2), (OC-6-31), further known as Ruthenate(2-), bis[[2,2'-bipyridine]-4,4'-dimethanesulfonato(2-)-κN1,κN1'][1-[4-(4'-methyl[2,2'-bipyridin]-4-yl-κN1,κN1')-1-oxobutoxy]-2,5-pyrrolidinedione]-, disodium, (OC-6-31)-(9CI));

BPRuUEEK-suberate-OSu (=CAS Reg. Number 406218-59-5 also known in the art as Ru(bpy)2-bpyCO-UEEK-suberate-OSu or Ruthenate(3-), bis(2,2'-bipyridine-κN1, κN1')[N-[4-(4'-methyl[2,2'-bipyridin]-4-yl-κN1,κN1')-1-oxobutyl]-β-alanyl-L-α-glutamyl-L-α-glutamyl-N6-[8-[(2,5-dioxo-1-pyrrolidinyl)oxy]-1,8-dioxooctyl]-L-lysinato (3-)]-, (OC-6-33)-(9CI)), which is a BPRu-label with a peptide linker, U=beta-alanine, E=glutaminic acid, K=lysine;

BPRu-(UE)-25-K-suberate-OSu (=the suberate N-Hydroxysuccinimide ester derivative of CAS Reg. Number 406679-88-7, also known in the art as Ruthenate(24-), bis(2,2'-bipyridine-κN1,κN1') [N-[4-(4'-methyl[2,2'-bipyridin]-4-yl-κN1,κN1')-1-oxobutyl]-(UE)25-L-lysinato(26-)]-, (OC-6-33)-(9CI)), with U=β-alanyl, E=L-α-glutamyl;

BPRu2-SK2-suberate-OSu (=the suberate N-Hydroxysuccinimide ester derivative of CAS Reg. Number 406218-60-8, also known in the art as Ruthenate(7-), bis(2,2'-bipyridine-κN1,κN1')[N-[4-(4'-methyl[2,2'-bipyridin]-4-yl-κN1,κN1')-1-oxobutyl]-β-alanyl-N6-(N-acetyl-(EU)3)-L-lysyl-N6-(N-acetyl-(EU)3)-L-lysyl-(UE)2-L-lysinato(9-)]-, nonahydrogen (9CI)), with U=β-alanyl, E=L-α-glutamyl; 4,4',5',5-tetramethyl bipyridine Re(I)(4-ethyl pyridine) $(CO)_3{}^{30}$ $CF_3SO_3{}^-$, and Pt(2-(2-thienyl)pyridine)$_2$.

Further known chelates are bis[(4,4'-carbomethoxy)-2,2'-bipyridine]-2-[3-(4-methyl-2,2'-bipyridine-4-yl)propyl]-1,3-dioxolane ruthenium (II); bis(2,2'bipyridine)[4-(butan-1-al)-4'-methyl-2,2'-bipyridine] ruthenium (II); bis(2,2'-bipyridine)[4-(4'-methyl-2,2'-bipyridine-4'-yl)-butyric acid] ruthenium (II); (2,2'-bipyridine)[bis-bis(1,2-diphenylphosphino)ethylene]2-[3(4-methyl-2,2'-bipyridine-4'-yl)propyl]-1,3-di-oxolane osmium (II); bis(2,2'-bipyridine)[4-(4'-methyl-2,2'-bipyridine)-butylamine]ruthenium (II); bis(2,2'-bipyridine)[1-bromo-4-(4'-methyl-2,2'-bipyridine-4-yl)-butane] ruthenium (II); and bis(2,2'-bipyridine) maleimidohexanoic acid, 4-methyl-2,2'-bipyridine-4'-butylamide ruthenium (II). In an embodiment, the ECL compound comprising a transition metal complex is tris(2,2'-bipyridyl) ruthenium $(Ru(bpy)_3{}^{2+}$, also known as Ru(bpy) or derivatives thereof like (BPRu=Ru(bpy)2-bpyCO-OSu), (Sulfo-BPRu NHS Ester).

In a further embodiment, the ECL compound is selected from the group consisting of BPRu (=Ru(bpy)2-bpyCO-OSu); Sulfo-BPRu NHS Ester; BPRuUEEK-suberate-OSu; BPRu-(UE)-25-K-suberate-OSu and BPRu2-SK2-suberate-OSu.

It is known to a person skilled in the art that also hydrophilic derivatives of the aforesaid ECL compounds can be used. Therefore in an further embodiment the term ECL compound also includes hydrophilic derivatives of the aforesaid ECL compounds.

In a further embodiment, the ECL compound comprising a transition metal complex is an Ir-complex as disclosed in WO 2014/019707 (A2), in an embodiment is an Ir(6-phenylphenanthridine)2-pyridine-2-carboxylic acid or a derivative thereof, including, e.g. Ir(6-phenylphenanthridine)2-3-Hydroxypyridine-2-carboxylic acid, Ir(6-phenylphenanthridine)$_2$-4-(Hydroxymethyl)pyridine-2-carboxylic acid, Ir(6-phenylphenanthridine)$_2$-2-(Carboxyethylphenyl)pyridine-2-carboxylic acid Ir(6-phenylphenanthridine)$_2$-5-(Methoxy)pyridine-2-carboxylic acid, or an Ir(6-phenylphenanthridine)$_2$-2-(Carboxyethylphenyl)pyridine-2-carboxylic acid ester, or derivatives of it like iridium complexes with ligands substituted with one or more sulfonic acids or iridium complexes as described in WO2012107419 (A1), WO2012107420 (A1), WO2014019707 (A2), WO2014019708 (A1), WO2014019709 (A2), WO2014019710 (A1), WO2014019711 (A1).

In a further embodiment the ECL compound comprising a transition metal complex is CAS Registry Number 1556730-07-4 (=IB3/47, also known in the art as Iridate(3-), [5-[4-(2-carboxyethyl)phenyl]-2-pyridinecarboxylato(2-)-κN1,κO2] bis [2-(6-phenanthridinyl-κN)-5-(3-sulfonatopropoxy)phenyl-κC]-, cesium hydrogen (1:2:1) or the N-hydroxy succinimde ester thereof.

In an further embodiment the ECL compound comprising a transition metal complex is a Iridium complexes with two phenyl-phenanthridine ligands having two sulfonato-propoxy substituents, two sulfo-methyl, comprising 2,9-Phenanthridinedimethanesulfonic acid, 6-phenyl-, sodium salt (CAS Registry Number 1554465-50-7) or two polyethylenglycol substituents, or three of each, or combinations thereof.

In an further embodiment with Ruthenium complexes different linkers can be used like (UE)25, or polyethylene glycol, or others.

In an embodiment, the compound comprising a transition metal complex is a detection reagent comprising an analyte specific reagent and a label. The term "analyte specific reagent" (ASR) according to the present invention has to be understood as a molecule or biomolecule (e.g. a protein or antibody) with the capability to specifically bind the analyte. "Analyte specific reagents" (ASRs) are a class of biological molecules which can be used to identify and measure the amount of an individual chemical substance in biological specimens. ASRs are for example antibodies, both polyclonal and monoclonal, specific receptor proteins, ligands, nucleic acid sequences, and similar reagents which, through specific binding or chemical reaction with substances in a specimen, are intended to use in a diagnostic application for identification and quantification of an individual chemical substance or ligand in biological specimens. An ASR will fulfill both, the criteria for affinity as well as for specificity of binding the analyte. Certain analytes are of high medical and diagnostic relevance even at concentrations in the sub-picomolar range. Especially the group of infectious disease parameters such as hepatitis virus B soluble antigen (HBsAg), human immunodeficiency virus antigen (HIVAg), hepatitis C virus antigen (HCVAg), in particular hepatitis C virus core antigen (HCVcAg) and cardiac markers such as Troponin-T (TnT) are examples of such analytes. Especially in these cases, improving the sensitivity is of major medical value for the patient.

The term "antibody" is used in the broadest sense and specifically includes monoclonal antibodies (including full length monoclonal antibodies), polyclonal antibodies, multispecific antibodies (e.g., bispecific antibodies), antibody fragments, single-chain antibodies, nanobodies, and the like. The term "antibody" encompasses the various forms of antibody structures including whole antibodies and antibody fragments. The antibody according to the invention is in one embodiment a human antibody, a humanized antibody, a chimeric antibody, an antibody derived form other animal species like mouse, goat or sheep, a monoclonal or polyconal antibody, or a T cell antigen depleted antibody. Genetic engineering of antibodies is e.g. described in Morrison, S. L., et al., Proc. Natl. Acad Sci. USA 81 (1984) 6851-6855; U.S. Pat. No. 5,202,238 and US 5,204,244; Riechmann, L., et al., Nature 332 (1988) 323-327; Neuberger, M. S., et al., Nature 314 (1985) 268-270; Lonberg, N., Nat. Biotechnol. 23 (2005) 1117-1125.

Any antibody fragment retaining the above criteria of a analyte specific reagent can be used. Antibodies are generated by state of the art procedures, e.g., as described in Tijssen (Tijssen, P., Practice and theory of enzyme immunoassays, 11, Elsevier Science Publishers B.V., Amsterdam, the whole book, especially pages 43-78). In addition, the skilled artisan is well aware of methods based on immunosorbents that can be used for the specific isolation of antibodies. By these means the quality of antibodies and hence their performance in immunoassays can be enhanced (Tijssen, P., supra, pages 108-115).

A "detection reagent" according to the present invention comprises an analyte specific reagent (ASR) labeled with an electrochemiluminescent group, or an analyte homolog labeled with an electrochemiluminescent group. Depending on the test format, it is known to the skilled artisan, which type of detection reagent has to be selected for the various assay formats (e.g. sandwich assay, double antigen bridging assay (DAGS), competitive assay, homogeneous assay, heterogeneous assay). A detection reagent in a heterogeneous immunoassay might be for example a labeled antibody. It is known to a person skilled in the art that the detection reagent can be immobilized on a solid phase. In an embodiment the method for measuring an analyte in a sample via electrochemiluminescent detection can be performed as a homogeneous assay. In an embodiment the method can be performed as a heterogeneous assay. In an embodiment the method can be performed in a sandwich assay format. In an embodiment the method can be performed in a competetive assay format. Also in an embodiment the method can be performed in a double antigen bridging assay format (DAGS). Known immunoassay formats are described in detail in the book of Price, C. P. and Newman, D. J., Principles and Practice of Immunoassay, 2nd ed. (1997).

The term "branched-chain tertiary amine", as used herein, relates to a tertiary amine comprising at least one alkyl chain having a secondary carbon atom in the alpha-position of the alkyl chain, i.e. to a tertiary amine comprising at least one 1-branched alkyl chain. As used herein, the C-alpha atom of a side chain of a tertiary amine is the carbon atom covalently bonded to the central nitrogen atom. Thus, in an embodiment, the branched-chain tertiary amine is an alpha-branched-chain tertiary amine. In an embodiment, the branched-chain tertiary amine has the general structure of formula (I)

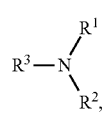

(I)

wherein
at least one of $R^1$, $R^2$, and $R^3$, in an embodiment one or two of $R^1$, $R^2$, and $R^3$ are independently selected side chains according to formula (II)

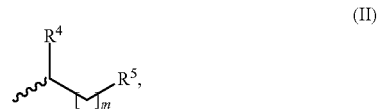

(II)

wherein
m is 0, 1, or 2, in an embodiment is 0 or 1;
$R^4$ is alkyl, in an embodiment is straight-chain $C_1$-$C_3$ alkyl, in a further embodiment is ethyl or methyl, in another embodiment is methyl,
$R^5$ is alkyl, in an embodiment is straight-chain C1-C3 alkyl, in another embodiment is ethyl or methyl, in an embodiment is methyl,
and wherein the residual groups $R^1$, $R^2$, and $R^3$ are independently selected from alkyl, in a further embodiment are independently selected from straight-chain alkyl, in another embodiment are independently selected from the group consisting of n-pentyl, n-butyl, n-propyl, ethyl and methyl, in an embodiment are independently selected from n-propyl, ethyl, and methyl.

As used herein, the terms "chemical compound", "salt", and "solvate" are used in their usual meaning known to the skilled chemist. If the net charge of a compound according to the present invention is positive, in an embodiment counterions are trifluoromethanesulfonate (triflate), sulfate, alkyl sulfonate, tosylate, phosphate, tetrafluoroborate, hexafluorophosphate, trifluoracetate, perchlorate, chloride or nitrate ions. If the net charge of a compound according to the present invention is negative, in an embodiment counterions are lithium, sodium, and/or potassium ions, or tetramethlyammonium ions. In an embodiment, the net charge of a compound according to the present invention is the net charge of the compound in aqueous solution under standard conditions as specified elsewhere herein.

The term "side chain" is understood by the skilled person and relates to an atom or chemical group attached covalently to the core part of a chemical compound as described herein, said core part also being referred to as "main chain" or "backbone". In an embodiment, the side chain is an organic side chain as described herein below. The term "substituted" side chain relates to a side chain substituted at one or more positions, in an embdoment, at 1, 2, or 3 positions, wherein substituents may be attached at any available atom to produce a stable chemical compound. It is understood by the skilled person that the term "optionally substituted" side chain relates to an unsubstituted or to a substituted side chain.

The term "organic side chain", as used herein, relates to any, optionally substituted, side chain comprising at least one carbon atom. The term "alkyl", as used herein, relates to a straight or branched chain, saturated hydrocarbon group, linked to the main chain or to the central nitrogen of the tertiary amine by a covalent bond to at least one of its at least one carbon atoms. Examples of alkyl groups are straight chain alkyls, e.g., methyl, ethyl, n-propyl, n-butyl, n-pentyl, or branched chain alkyl groups, e.g., —CH(CH$_3$)$_2$, —CH(CH$_2$CH$_3$)$_2$, —CH(CH$_3$)(CH$_2$CH$_3$). Accordingly, alkyl groups include primary alkyl groups, secondary alkyl groups, and tertiary alkyl groups; in an embodiment, alkyl groups are primary alkyl groups or secondary alkyl groups.

In a further embodiment, at least one of the residual groups $R^1$, $R^2$, and $R^3$ which are not selected according to formula (II) is straight-chain alkyl, in an embodiment is selected from the group consisting of n-pentyl, n-butyl, n-propyl, ethyl or methyl, in further embodiment is propyl, ethyl, or methyl. In a further embodiment, all of the residual groups $R^1$, $R^2$, and $R^3$ which are not selected according to formula (II) are straight-chain alkyl, in an embodiment are selected from the group consisting of n-pentyl, n-butyl, n-propyl, ethyl or methyl, in further embodiment is propyl, ethyl, or methyl.

In a further embodiment, the branched-chain tertiary amine is a compound according to the general formula (III):

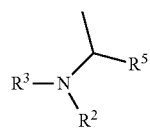

(III)

with $R^2$ and $R^3$ being selected independently from the group consisting of methyl, ethyl, n-propyl, and n-pentyl; and $R^5$ being selected from methyl, ethyl, and n-propyl. In a further embodiment, the branched-chain tertiary amine is a compound according to the aforesaid general formula (III) with $R^2$ and $R^3$ being selected independently from the group consisting of methyl, ethyl, n-propyl, n-butyl, and n-pentyl; and $R^5$ being selected from methyl, ethyl, and n-propyl. Thus, in an embodiment, the branched-chain tertiary amine is one of the compounds of Table 1. In a further embodiment, the branched-chain tertiary amine is one of the compounds of Table 1 or one of compounds 46 to 60 of Table 2.

In a further embodiment, the branched-chain tertiary amine is a compound according to the general formula (IV):

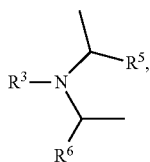

(IV)

with $R^3$ being selected from the group consisting of methyl, ethyl, n-propyl, and n-pentyl, and $R^5$ and $R^6$ being selected independently from methyl, ethyl, and n-propyl. In a further embodiment, the branched-chain tertiary amine is a compound according to the aforesaid general formula (IV) with $R^3$ being selected from the group consisting of methyl, ethyl, n-propyl, n-butyl, and n-pentyl, and $R^5$ and $R^6$ being selected independently from methyl, ethyl, and n-propyl. Thus, in an embodiment, the branched-chain tertiary amine is one of the compounds of Table 2. In a further embodiment, the branched-chain tertiary amine is one of compounds 31 to 45 or 61 to 75 of Table 2.

In a further embodiment, the branched-chain tertiary amine is a compound according to the general formula (V):

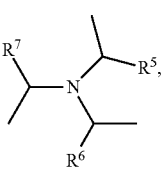

(V)

with $R^5$, $R^6$, and $R^7$ being selected independently from methyl, ethyl and n-propyl. Thus, in an embodiment, the branched-chain tertiary amine is one of the compounds of Table 3.

In a further embodiment, the branched-chain tertiary amine is a compound according to the general formula (VI):

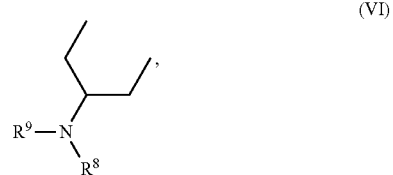

(VI)

with $R^8$ and $R^9$ being independently selected from methyl, ethyl, n-propyl, n-butyl, n-pentyl, isopropyl, sec-butyl (1-methylpropyl), sec-pentyl (1-methylbutyl), and 3-pentyl (1-ethylpropyl). Thus, in an embodiment, the branched-chain tertiary amine is one of the compounds of Table 4.

In a further embodiment, the branched-chain tertiary amine is a compound according to the general formula (VII):

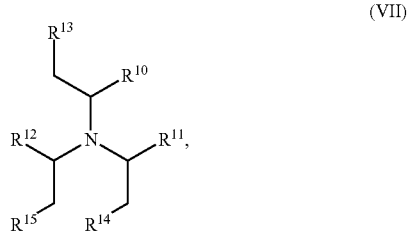

(VII)

wherein $R^{10}$ to $R^{15}$ are independently selected from —H and methyl, wherein at least one of $R^{10}$ to $R^{12}$ is methyl; and wherein if $R^{10}$, $R^{11}$ and $R^{12}$ are methyl, at least one of $R^{13}$ to $R^{15}$ is methyl. Thus, in an embodiment, the branched-chain tertiary amine is compound No: 6, 7, 10, 21, 22, 25, 32, 33, 36, 37, 38, 38, 42, 43,76, 78, or 81 of Tables 1 to 4.

In an embodiment, the branched-chain tertiary amine is N,N-Dipropyl-N-(sec-butyl)amine (also known under its trivial name "Dipropyl-isobutylamine" or "DPIBA", CAS 60021-91-2, compound No: 25 of Table 1), N,N-Di(sec-butyl)-propylamine (also known under its trivial name "Diisobutyl-propylamine" or "DIBPA", compound No: 43 of Table 2), or N,N-Diisopropyl-N-ethylamine (DIEA, CAS 7087-68-5, compound No: 32 of Table 2). In a further embodiment, the branched-chain tertiary amine is N,N-Dipropyl-N-(sec-butyl)amine or N,N-Di(sec-butyl)-N-propylamine. In a further embodiment, the branched-chain tertiary amine is N,N-Di(sec-butyl)-N-propylamine.

TABLE 1 embodiments of di(n-alkyl)-(1-methyl-alkyl)amines, substituents relate to formula (I)

| compound No | R1 | R2 | R3 |
|---|---|---|---|
| 1 | isopropyl | methyl | methyl |
| 2 | isopropyl | methyl | ethyl |
| 3 | isopropyl | methyl | n-propyl |
| 4 | isopropyl | methyl | n-butyl |

TABLE 1-continued embodiments of di(n-alkyl)-(1-methyl-alkyl)amines, substituents relate to formula (I)

| compound No | R1 | R2 | R3 |
|---|---|---|---|
| 5 | isopropyl | methyl | n-pentyl |
| 6 | isopropyl | ethyl | ethyl |
| 7 | isopropyl | ethyl | n-propyl |
| 8 | isopropyl | ethyl | n-butyl |
| 9 | isopropyl | ethyl | n-pentyl |
| 10 | isopropyl | n-propyl | n-propyl |
| 11 | isopropyl | n-propyl | n-butyl |
| 12 | isopropyl | n-propyl | n-pentyl |
| 13 | isopropyl | n-butyl | n-butyl |
| 14 | isopropyl | n-butyl | n-pentyl |
| 15 | isopropyl | n-pentyl | n-pentyl |
| 16 | sec-butyl (1-methylpropyl) | methyl | methyl |
| 17 | sec-butyl (1-methylpropyl) | methyl | ethyl |
| 18 | sec-butyl (1-methylpropyl) | methyl | n-propyl |
| 19 | sec-butyl (1-methylpropyl) | methyl | n-butyl |
| 20 | sec-butyl (1-methylpropyl) | methyl | n-pentyl |
| 21 | sec-butyl (1-methylpropyl) | ethyl | ethyl |
| 22 | sec-butyl (1-methylpropyl) | ethyl | n-propyl |
| 23 | sec-butyl (1-methylpropyl) | ethyl | n-butyl |
| 24 | sec-butyl (1-methylpropyl) | ethyl | n-pentyl |
| 25 | sec-butyl (1-methylpropyl) | n-propyl | n-propyl |
| 26 | sec-butyl (1-methylpropyl) | n-propyl | n-butyl |
| 27 | sec-butyl (1-methylpropyl) | n-propyl | n-pentyl |
| 28 | sec-butyl (1-methylpropyl) | n-butyl | n-butyl |
| 29 | sec-butyl (1-methylpropyl) | n-butyl | n-pentyl |
| 30 | sec-butyl (1-methylpropyl) | n-pentyl | n-pentyl |

TABLE 2 embodiments of (n-alkyl)-di(1-methyl-alkyl)amines and tertiary sec-pentyl-amines; substituents relate to formula (I)

| compound No | R1 | R2 | R3 |
|---|---|---|---|
| 31 | isopropyl | isopropyl | methyl |
| 32 | isopropyl | isopropyl | ethyl |
| 33 | isopropyl | isopropyl | n-propyl |
| 34 | isopropyl | isopropyl | n-butyl |
| 35 | isopropyl | isopropyl | n-pentyl |
| 36 | sec-butyl (1-methylpropyl) | isopropyl | methyl |
| 37 | sec-butyl (1-methylpropyl) | isopropyl | ethyl |
| 38 | sec-butyl (1-methylpropyl) | isopropyl | n-propyl |
| 39 | sec-butyl (1-methylpropyl) | isopropyl | n-butyl |
| 40 | sec-butyl (1-methylpropyl) | isopropyl | n-pentyl |
| 41 | sec-butyl (1-methylpropyl) | sec-butyl (1-methylpropyl) | methyl |
| 42 | sec-butyl (1-methylpropyl) | sec-butyl (1-methylpropyl) | ethyl |
| 43 | sec-butyl (1-methylpropyl) | sec-butyl (1-methylpropyl) | n-propyl |
| 44 | sec-butyl (1-methylpropyl) | sec-butyl (1-methylpropyl) | n-butyl |
| 45 | sec-butyl (1-methylpropyl) | sec-butyl (1-methylpropyl) | n-pentyl |
| 46 | sec-pentyl (1-methylbutyl) | methyl | methyl |
| 47 | sec-pentyl (1-methylbutyl) | methyl | ethyl |
| 48 | sec-pentyl (1-methylbutyl) | methyl | n-propyl |
| 49 | sec-pentyl (1-methylbutyl) | methyl | n-butyl |
| 50 | sec-pentyl (1-methylbutyl) | methyl | n-pentyl |
| 51 | sec-pentyl (1-methylbutyl) | ethyl | ethyl |
| 52 | sec-pentyl (1-methylbutyl) | ethyl | n-propyl |
| 53 | sec-pentyl (1-methylbutyl) | ethyl | n-butyl |
| 54 | sec-pentyl (1-methylbutyl) | ethyl | n-pentyl |
| 55 | sec-pentyl (1-methylbutyl) | n-propyl | n-propyl |
| 56 | sec-pentyl (1-methylbutyl) | n-propyl | n-butyl |
| 57 | sec-pentyl (1-methylbutyl) | n-propyl | n-pentyl |
| 58 | sec-pentyl (1-methylbutyl) | n-butyl | n-butyl |
| 59 | sec-pentyl (1-methylbutyl) | n-butyl | n-pentyl |
| 60 | sec-pentyl (1-methylbutyl) | n-pentyl | n-pentyl |
| 61 | sec-pentyl (1-methylbutyl) | isopropyl | methyl |
| 62 | sec-pentyl (1-methylbutyl) | isopropyl | ethyl |
| 63 | sec-pentyl (1-methylbutyl) | isopropyl | n-propyl |
| 64 | sec-pentyl (1-methylbutyl) | isopropyl | n-butyl |
| 65 | sec-pentyl (1-methylbutyl) | isopropyl | n-pentyl |
| 66 | sec-pentyl (1-methylbutyl) | sec-butyl (1-methylpropyl) | methyl |
| 67 | sec-pentyl (1-methylbutyl) | sec-butyl (1-methylpropyl) | ethyl |
| 68 | sec-pentyl (1-methylbutyl) | sec-butyl (1-methylpropyl) | n-propyl |
| 69 | sec-pentyl (1-methylbutyl) | sec-butyl (1-methylpropyl) | n-butyl |
| 70 | sec-pentyl (1-methylbutyl) | sec-butyl (1-methylpropyl) | n-pentyl |
| 71 | sec-pentyl (1-methylbutyl) | sec-pentyl (1-methylbutyl) | methyl |
| 72 | sec-pentyl (1-methylbutyl) | sec-pentyl (1-methylbutyl) | ethyl |
| 73 | sec-pentyl (1-methylbutyl) | sec-pentyl (1-methylbutyl) | n-propyl |
| 74 | sec-pentyl (1-methylbutyl) | sec-pentyl (1-methylbutyl) | n-butyl |
| 75 | sec-pentyl (1-methylbutyl) | sec-pentyl (1-methylbutyl) | n-pentyl |

TABLE 3 embodiments of tri(1-methyl-alkyl)amines; substituents relate to formula (I)

| compound No | R1 | R2 | R3 |
|---|---|---|---|
| 76 | isopropyl | isopropyl | sec-butyl (1-methylpropyl) |
| 77 | isopropyl | isopropyl | sec-pentyl (1-methylbutyl) |
| 78 | sec-butyl (1-methylpropyl) | isopropyl | sec-butyl (1-methylpropyl) |
| 79 | sec-butyl (1-methylpropyl) | isopropyl | sec-pentyl (1-methylbutyl) |
| 80 | sec-pentyl (1-methylbutyl) | isopropyl | sec-pentyl (1-methylbutyl) |
| 81 | sec-butyl (1-methylpropyl) | sec-butyl (1-methylpropyl) | sec-butyl (1-methylpropyl) |
| 82 | sec-butyl (1-methylpropyl) | sec-butyl (1-methylpropyl) | sec-pentyl (1-methylbutyl) |
| 83 | sec-pentyl (1-methylbutyl) | sec-pentyl (1-methylbutyl) | sec-pentyl (1-methylbutyl) |

TABLE 4 embodiments of tertiary (1-ethyl-alkyl)-amines:

| compound No | R1 | R2 | R3 |
|---|---|---|---|
| 84 | 3-pentyl (1-ethylpropyl) | methyl | methyl |
| 85 | 3-pentyl (1-ethylpropyl) | methyl | ethyl |
| 86 | 3-pentyl (1-ethylpropyl) | methyl | n-propyl |
| 87 | 3-pentyl (1-ethylpropyl) | methyl | n-butyl |
| 88 | 3-pentyl (1-ethylpropyl) | methyl | n-pentyl |
| 89 | 3-pentyl (1-ethylpropyl) | ethyl | ethyl |
| 90 | 3-pentyl (1-ethylpropyl) | ethyl | n-propyl |
| 91 | 3-pentyl (1-ethylpropyl) | ethyl | n-butyl |
| 92 | 3-pentyl (1-ethylpropyl) | ethyl | n-pentyl |
| 93 | 3-pentyl (1-ethylpropyl) | n-propyl | n-propyl |
| 94 | 3-pentyl (1-ethylpropyl) | n-propyl | n-butyl |
| 95 | 3-pentyl (1-ethylpropyl) | n-propyl | n-pentyl |
| 96 | 3-pentyl (1-ethylpropyl) | n-butyl | n-butyl |
| 97 | 3-pentyl (1-ethylpropyl) | n-butyl | n-pentyl |
| 98 | 3-pentyl (1-ethylpropyl) | n-pentyl | n-pentyl |
| 99 | 3-pentyl (1-ethylpropyl) | isopropyl | methyl |
| 100 | 3-pentyl (1-ethylpropyl) | isopropyl | ethyl |
| 101 | 3-pentyl (1-ethylpropyl) | isopropyl | n-propyl |
| 102 | 3-pentyl (1-ethylpropyl) | isopropyl | n-butyl |
| 103 | 3-pentyl (1-ethylpropyl) | isopropyl | n-pentyl |
| 104 | 3-pentyl (1-ethylpropyl) | sec-butyl (1-methylpropyl) | methyl |
| 105 | 3-pentyl (1-ethylpropyl) | sec-butyl (1-methylpropyl) | ethyl |
| 106 | 3-pentyl (1-ethylpropyl) | sec-butyl (1-methylpropyl) | n-propyl |
| 107 | 3-pentyl (1-ethylpropyl) | sec-butyl (1-methylpropyl) | n-butyl |
| 108 | 3-pentyl (1-ethylpropyl) | sec-butyl (1-methylpropyl) | n-pentyl |
| 109 | 3-pentyl (1-ethylpropyl) | sec-pentyl (1-methylbutyl) | methyl |
| 110 | 3-pentyl (1-ethylpropyl) | sec-pentyl (1-methylbutyl) | ethyl |
| 111 | 3-pentyl (1-ethylpropyl) | sec-pentyl (1-methylbutyl) | n-propyl |
| 112 | 3-pentyl (1-ethylpropyl) | sec-pentyl (1-methylbutyl) | n-butyl |
| 113 | 3-pentyl (1-ethylpropyl) | sec-pentyl (1-methylbutyl) | n-pentyl |
| 114 | 3-pentyl (1-ethylpropyl) | isopropyl | isopropyl |
| 115 | 3-pentyl (1-ethylpropyl) | isopropyl | sec-butyl (1-methylpropyl) |
| 116 | 3-pentyl (1-ethylpropyl) | isopropyl | sec-pentyl (1-methylbutyl) |
| 117 | 3-pentyl (1-ethylpropyl) | sec-butyl (1-methylpropyl) | sec-butyl (1-methylpropyl) |
| 118 | 3-pentyl (1-ethylpropyl) | sec-butyl (1-methylpropyl) | sec-pentyl (1-methylbutyl) |
| 119 | 3-pentyl (1-ethylpropyl) | sec-pentyl (1-methylbutyl) | sec-pentyl (1-methylbutyl) |
| 120 | 3-pentyl (1-ethylpropyl) | 3-pentyl (1-ethylpropyl) | sec-butyl (1-methylpropyl) |
| 121 | 3-pentyl (1-ethylpropyl) | 3-pentyl (1-ethylpropyl) | sec-pentyl (1-methylbutyl) |
| 122 | 3-pentyl (1-ethylpropyl) | 3-pentyl (1-ethylpropyl) | 3-pentyl (1-ethylpropyl) |

In a further embodiment, the branched-chain amine of the present invention is an amine which, when oxidized by an effective amount of electrochemical energy, forms a strong reducing agent ("Electrogenerated Chemiluminescence 69: The Tris(2,2'-bipyridine)ruthenium(II), (Ru(bpy)$_3$$^{2+}$)/Tri-n-propylamine (TPrA) System Revisited", Miao et al. (2002), Journal of the American Chemical Society 124(48):14478).

The term "composition" is known to the skilled person and relates to a, homogenous or inhomogenous, mixture of at least two chemical compounds. A "reagent composition" or "ECL-reagent composition" according to the present invention comprises reagents supporting ECL-signal generation, e.g. a coreactant, a buffering agent for pH control, and optionally other components. The skilled artisan is aware of components of a reagent composition which are required for ECL signal generation in electrochemiluminescent detection methods. Also, as used herein, the term "reaction mixture" relates to any mixture contacting a first compound with a second compound, e.g. a branched-chain tertiary amine and an ECL compound comprising a transition metal complex, allowing said first and second compound to react. In an embodiment, the reaction mixture additionally comprises a solvent, in an embodiment comprises water. In a further embodiment, the reaction mixture further comprises one or more auxiliary compounds, e.g. a buffer, a preservative, or a detergent, or any combination thereof. In an embodiment, the reaction mixture further comprises compounds as described in WO 2012055815 A1. In an embodiment, the reaction mixture is an aqueous solution. In an embodiment, a branched-chain tertiary amine according to the present invention is the only tertiary amine in the reaction mixture.

An "aqueous solution" as used herein is a homogeneous solution of substances or liquid compounds dissolved in water. An aqueous solution may also comprise organic solvents. Organic solvents are known to the person skilled in the art, e.g. methanol, ethanol or dimethylsulfoxid. As used herein it is also to be understood that an aqueous solution can comprise at most 50% organic solvents. As will be understood by the skilled person, the term aqueous solution, in an embodiment, includes an aqueous solution into which particles are dispersed, in an embodiment homogenously dispersed.

A species that participates with the ECL label in the ECL process is referred to herein as ECL "coreactant". Commonly used coreactants for ECL include tertiary amines (e.g. tripropylamine (TPA)), oxalate, and persulfate. The skilled artisan is aware of available coreactants useful for electrochemiluminescent detection methods. According to a specific embodiment the coreactant according to the present invention is a branched-chain tertiary amine.

The term "label" as used herein refers to any substance that is capable of producing a detectable electrochemiluminescent signal, whether visibly detectable or detecable by using suitable instrumentation. Various labels suitable for use in the present invention include, electrochemiluminescent compounds. In an embodiment, the label is a transition metal complex or a detection reagent as specified above.

An "electrochemiluminescence assay" or "ECLA" is an electrochemical assay in which an analyte molecule is detected by its binding to a detection reagent, which is linked to a label as specified above, and by inducing ECL to occur ("electrochemically triggering the release of luminescence"). In an embodiment, an electrode electrochemically initiates luminescence of the chemical label. In a further embodiment, ECL is triggered by applying a voltage to an electrode contacting a reagent composition. For detecting an ECL signal, light emitted by the ECL compound comprising a transition metal complex is measured by a photodetector, indicating the presence or quantity of bound analyte molecule/target molecule complexes. ECLA methods are described, for example, in U.S. Pat. Nos. 5,543,112; 5,935,779; and 6,316,607. Signal modulation can be maximized for different analyte molecule concentrations for precise and sensitive measurements.

In an embodiment, electrochemically triggering the release of luminescence comprises applying a measuring voltage at least 0.1 V lower, in an embodiment at least 0.2 V lower, in a further embodiment at least 0.3 V lower than the measuring voltage used in a comparable electrochemical assay using tripropylamine as coreactant. The term "comparable electrochemical assay", as used herein, relates to an electrochemical assay comprising the use of at least the same ECL reagent and the same working electrode as the electrochemical assay of the present invention. In an embodiment, a comparable electrochemical assay is an electrochemical assay comprising the same steps and reagents as the electrochemical assay of the present invention with the exception of the coreactand, which is a branched-chain tertiary amine according to the present invention, but TPA according to the comparable electrochemical assay. Thus, in an embodiment, electrochemically triggering the release of luminescence comprises applying a measuring voltage of from 0.7 V to 1.6 V, in an embodiment of from 0.8 V to 1.3 V, in a further embodiment of from 0.9 V to 1.1 V. According to the present invention, if not otherwise noted, potentials are measured versus a standard Ag/AgCl electrode, in an embodiment a Ag/AgCl electrode with saturated KCl at 25° C. In an embodiment, the electrode contacting the reaction electrode of the present invention, which is also referred to as working electrode, comprises or consists of platinum (=Pt), gold (=Au), or glassy carbon, in an embodiment comprises or consists of platinum. Thus, in a further embodiment, triggering the release of luminescence comprises applying a measuring voltage of from 0.8 V to 1.3 V, in a further embodiment of from 0.9 V to 1.1 V versus an Ag/AgCl electrode at a platinum, gold, or glassy carbon working electrode, in an embodiment at a platinum working electrode. In a further embodiment, the branched-chain amine is DIBPA and triggering the release of luminescence comprises applying a measuring voltage of from 0.8 V to 1.2 V, in a further embodiment of from 0.85 V to 1.1 V versus an Ag/AgCl electrode at a platinum, gold, or glassy carbon working electrode, in an embodiment at a platinum working electrode. In a further embodiment, the branched-chain amine is DPIBA and triggering the release of luminescence comprises applying a measuring voltage of from 0.8 V to 1.2 V, in a further embodiment of from 0.9 V to 1.1 V versus an Ag/AgCl electrode at a platinum, gold, or glassy carbon working electrode, in an embodiment at a platinum working electrode.

In an ECLA procedure, microparticles coated with detection reagent can be suspended in the sample to efficiently bind the analyte and/or to allow efficient retrieval of bound analyte. For example, the particles can have a diameter of 0.05 µm to 200 µm, 0.1 µm to 100 µm, or 0.5 µm to 10 µm, and a surface component capable of binding an analyte molecule. In one frequently used ECLA-system (Elecsys®, Roche Dagnsotics, Germany), the microparticles have a diameter of about 3 µm. The microparticles can be formed of crosslinked starch, dextran, cellulose, protein, organic polymers, styrene copolymer such as styrene/butadiene copolymer, acrylonitrile/butadiene/styrene copolymer, vinylacetyl acrylate copolymer, vinyl chloride/acrylate copolymer, inert inorganic particles, chromium dioxide, oxides of iron, silica, silica mixtures, proteinaceous matter, or mixtures thereof, including but not limited to sepharose beads, latex beads, shell-core particles, and the like. The microparticles are, in an embodiment, monodisperse, and can be magnetic, such as paramagnetic beads. See, for example, U.S. Pat. Nos. 4,628,037; 4,965,392; 4,695,393; 4,698,302; and 4,554,088. Microparticles can be used in an amount ranging from about 1 to 10,000 µg/ml, in an embodiment 5 to 1,000 µg/ml.

A "sample", as used according to the present invention, is obtained for the purpose of an in vitro evaluation. As the skilled artisan will appreciate, any such assessment is made in vitro. If the sample is a patient sample, it is discarded afterwards. In an embodiment, the patient sample is solely used for the in vitro diagnostic method of the invention and the material of the patient sample is not transferred back into the patient's body.

The embodiments of the invention can be used to test a sample for the presence of an analyte or an activity of interest. Such samples may be in solid, emulsion, suspension, liquid, or gas form. They may be, but are not limited to, samples containing or derived from human or animals, for example, cells (live or dead) and cell-derived products, immortalized cells, cell fragments, cell fractions, cell lysates, organelles, cell membranes, hybridoma, cell culture supernatants (including supernatants from antibody producing organisms such as hybridomas), waste or drinking water, food, beverages, pharmaceutical compositions, blood, serum, plasma, hair, sweat, urine, feces, stool, saliva, tissue, biopsies, effluent, separated and/or fractionated samples, separated and/or fractionated liquids, organs, plants, plant parts, plant byproducts, soil, water, water supply, water sources, filtered residue from fluids (gas and liquid), swipes, absorbent materials, gels, cytoskeleton, unfractionated samples, unfractionated cell lysates, cell nucleus/nuclei, nuclear fractions, chemicals, chemical solutions, structural biological components, skeletal (ligaments, tendons) components, separated and/or fractionated skeletal components, hair fractions and/or separations, skin, skin samples, skin fractions, dermis, endodermis, eukaryotic cells, prokaryotic cells, fungus, yeast, immunological cells, drugs, therapeutic drugs, oils, extracts, mucous, sewage, environmental samples, organic solvents or air. In an embodiment the sample can further comprise, for example, water, alcohols, acetonitrile, dimethyl sulfoxide, dimethyl formamide, n-methyl-pyrrolidone, methanol or other organic solvents.

In an embodiment, the sample is a sample of a bacterium, an archaebacterium, or a eukaryote. In an embodiment, the sample is a sample of a mammal, in an embodiment, of a sheep, goat, cow, horse, pig, guinea pig, mouse, rat, cat dog, or human. In a further embodiment, the sample is a sample of a human. In an embodiment, the sample is a sample of a body fluid, in an embodiment saliva, blood, plasma, serum, or urine; in an embodiment the sample is cell-free. In a further embodiment, the sample is a tissue or organ sample, or an extract derived therefrom.

Analytes that may be measured include, but are not limited to, whole cells, cell surface antigens, protein complexes, cell signaling factors and/or components, second messengers, second messenger signaling factors and/or components, subcellular particles (e.g., organelles or membrane fragments), viruses, prions, dust mites or fragments thereof, viroids, immunological factors, antibodies, antibody fragments, antigens, haptens, fatty acids, nucleic acids (and synthetic analogs), ribosomes, proteins (and synthetic analogs), lipoproteins, polysaccharides, inhibitors, cofactors, haptens, cell receptors, receptor ligands, lipopolysaccharides, glycoproteins, peptides, polypeptides, enzymes, enzyme substrates, enzyme products, nucleic acid processing enzymes (e.g., polymerases, nucleases, integrases, ligases, helicases, telomerases, etc.), protein processing enzymes (e.g., proteases, kinases, protein phophatases, ubiquitin-protein ligases, etc.), cellular metabolites, endocrine factors, paracrine factors, autocrine factors, cytokines, hormones, pharmacological agents, drugs, therapeutic drugs, synthetic organic molecules, organometallic molecules, tranquilizers, barbiturates, alkaloids, steroids, vitamins, amino acids, sugars, lectins, recombinant or derived proteins, biotin, avidin, streptavidin, or inorganic molecules present in the sample.

Analytes which are whole cells may be animal, plant, or bacterial cells, and may be viable or dead. Examples include plant pathogens such as fungi and nematodes. The term "subcellular particles" is meant to encompass, for example, subcellular organelles, membrane particles as from disrupted cells, fragments of cell walls, ribosomes, multi-enzyme complexes, and other particles which can be derived from living organisms. Nucleic acids include, for example, chromosomal DNA, plasmid DNA, viral DNA, and recombinant DNA derived from multiple sources. Nucleic acids also include RNAs, for example messenger RNAs, ribosomal RNAs and transfer RNAs. Polypeptides include, for example, enzymes, transport proteins, receptor proteins, and structural proteins such as viral coat proteins. In embodiments, polypeptides are enzymes and antibodies. In particular, polypeptides are monoclonal antibodies. Hormones include, for example, insulin and T4 thyroid hormone. Pharmacological agents include, for example, cardiac glycosides. It is, in an embodiment, within the scope of this invention to include synthetic substances which chemically resemble biological materials, such as synthetic polypeptides, synthetic nucleic acids, and synthetic membranes, vesicles and liposomes. The foregoing is not intended to be a comprehensive list of the biological substances suitable for use in this invention, but is meant only to illustrate the wide scope of the invention.

Also, typically, the analyte of interest is present at a concentration of $10^{-3}$ molar or less, for example, at least as low as $10^{-18}$ molar.

The expression "of interest" denotes an analyte or a substance of possible relevance that shall be analyzed or determined.

A "solid phase", also known as "solid support", is insoluble, functionalized, polymeric material to which detection reagents or other reagents may be attached or covalently bound (often via a linker) to be immobilized or allowing them to be readily separated (by filtration, centrifugation, washing etc.) from excess reagents, soluble reaction by-products, or solvents. Solid phases for the method according to the invention are widely described in the state of the art (see, e.g., Butler, J. E., Methods 22 (2000) 4-23). The term "solid phase" means a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes, chips or other spectrometer sample containers. A solid phase component of an assay is distinguished from inert solid surfaces with which the assay may be in contact in that a "solid phase" contains at least one moiety on its surface, which is intended to interact with the detection reagent. A solid phase may be a stationary component, such as a tube, strip, cuvette, chip or microtiter plate, or may be a non-stationary component, such as beads and microparticles. Microparticles can also be used as a solid phase for homogeneous assay formats. A variety of microparticles that allow either non-covalent or covalent attachment of proteins and other substances may be used. Such particles include polymer particles such as polystyrene and poly(methylmethacrylate); gold particles such as gold nanoparticles and gold colloids; and ceramic particles such as silica, glass, and metal oxide particles. See for example Martin, C. R., et al., Analytical Chemistry-News & Features (1998) 322A-327A, which is incorporated herein by reference.

The terms "chip", "bio-chip", "polymer-chip" or "protein-chip" are used interchangeably and refer to a collection of a large number of probes, markers or biochemical markers arranged on a shared substrate (e.g. a solid phase) which could be a portion of a silicon wafer, a nylon strip, a plastic strip, or a glass slide.

In an embodiment, the present invention relates to a method of detecting an electrochemiluminescence (ECL) signal comprising
   a) contacting a reaction composition comprising
      i) at least one branched-chain tertiary amine and
      ii) an ECL compound comprising a transition metal complex with an electrode,
   b) electrochemically triggering the release of luminescence, and
   c) detecting the ECL signal, In a further embodiment, the present invention concerns a method for detecting an analyte in a sample via electrochemiluminescence detection, comprising the steps of:
a) incubating the sample with a detection reagent labeled with an electrochemiluminescent group comprising a transition metal complex, in an embodiment comprising a tris(2,2'-bipyridyl)ruthenium complex $(Ru(bpy)_3^{2+})$,
b) separating analyte-bound and analyte-free labeled detection reagent,
c) contacting the separated analyte-bound labeled detection reagent with a branched-chain tertiary amine of the invention and with an electrode,
d) electrochemically triggering the release of luminescence, and
e) detecting the electrochemiluminescence (ECL) signal thereby detecting the analyte.

In a further embodiment, the present invention relates to a method for detecting an analyte in a sample via electrochemiluminescence detection, comprising the steps of:
a) incubating the sample with a detection reagent labeled with an electrochemiluminescent group comprising a transition metal complex, in an embodiment comprising $Ru(bpy)_3^{2+}$,
b) separating analyte-bound and analyte-free labeled detection reagent,
c) detecting ECL according to the method of the invention, with the detection reagent being the compound comprising a transition metal complex, and
d) detecting the analyte based on the result of the ECL detection in step c).

An aspect of the invention relates to improved ECL methods based on the reagent compositions of the present invention, particularly ECL methods featuring low detection limits. The reagent compositions comprising the branched-chain tertiary amines of the present invention surprisingly enable drastically reducing system background. More specifically, the methods of the invention provide improved sensitivity at low detection levels by reducing the background electrochemiluminescence in the absence of ECL labels.

The inventors have surprisingly discovered that the use of certain compounds from the group of branched-chain tertiary amine as coreactants in ECL reactions provides a number of advantages, such as reduced oxidation potential of said compounds, and an improved signal/background (S/BG) ratio in ECL detection methods and thus improved ECL assay performance.

A feature of the invention are methods for the determination of an analyte in a sample to be investigated using an electrochemiluminescent label, wherein one of the following listed methods for measuring electrochemiluminescent phenomena is employed.

Surprisingly the methods using compounds selected from the group of branched-chain tertiary amines emit less background luminescence than conventional test reagents without these compounds. This is particularly an advantage at low detection levels where increasing the signal to background ratio (=signal to noise ratio) greatly improves the sensitivity. Surprisingly, the inventors have found that performing an electrochemiluminescent detection using a method according to the present invention results in an improved signal to noise ratio of ECL detection.

The method for measuring an analyte in a sample via electrochemiluminescent detection according to the present invention can be performed, in an embodiment, in an aqueous solution.

In an embodiment the branched-chain tertiary amine used in the method is selected from the group consisting of is N,N-Dipropyl-N-(sec-butyl)amine (DPIBA), N,N-Di(sec-butyl)-N-propylamine (DIBPA), or N,N-Diisopropyl-N-ethylamine (DIEA), in an embodiment, is DPIBA or DIBPA, in a further embodiment is DPIBA, in a further embodiment is DIBPA.

For the avoidance of doubt, in an embodiment, the branched-chain tertiary amine is not tripropyl amine, triethanol amine, triethyl amine 1,4-piperazine-bis(ethanesulfonic acid), 1-piperidine ethanol, 1,4-diazabicyclo(2.2.2) octane, triisopropyl amine, or dibutyl ethanolamine.

In an embodiment, the branched-chain tertiary amine is used in the method in a concentration of at least 50 mM (i.e. 50 mmol/l), in a further embodiment in a concentration of at most 500 mM, in a further embodiment in a concentration of 50 mM to 500 mM, in a further embodiment in a concentration of 75 mM to 350 mM, in a further embodiment in a concentration of 100 mM to 250 mM.

In an embodiment the method according to the present invention is particularly well suited to detect biomolecules, such as proteins, polypeptides, peptides, peptidic fragments, hormones, peptid hormones, vitamins, provitamins, vitamin metabolites and amino acids in a sample of interest. In a further embodiment, the method according to the present invention is particularly well suited to detect biomolecules from the further classes of steroids, drugs, and therapeutics.

The sample used in the methods according to the present invention is in an embodiment a liquid sample, e.g., whole blood, serum or plasma. The sample, or more specific the sample of interest, in an embodiment may comprise any body fluid and stool. In an embodiment the sample will be a liquid sample like saliva, stool extracts, urine, whole blood, plasma or serum. In an embodiment the sample will be whole blood, plasma or serum.

It is known to a person skilled in the art that, in an embodiment, all steps in the methods of the present invention can be performed in the same location, e.g. in the same reaction vessel. Said steps may also be performed in an automatic process controlled by a control means.

Unspecific sample components and analyte-free labeled detection reagent can be removed in a separation process. For example, analyte-bound and analyte-free labeled detection reagent can be separated using a washing step. The analyte-bound labeled detection reagent is then incubated to perform the ECL detection of the method.

Also other test components supporting the electrochemiluminescent detection of an analyte may be used in the methods according to the present invention.

It has been found by the inventors that the background (BG) generated by tertiary amines is an exponential function of the voltage applied for their oxidation. Furthermore the inventors found that branched-chain tertiary amines exhibit an oxidation potential significantly lower as compared to unbranched analogues, in particular tripropylamine (TPA). Accordingly the inventors found, that a method for measuring an analyte in a sample via electrochemiluminescent detection using branched-chain tertiary amines requires a reduced oxidation potential, improving signal to noise ratio (S/BG ratio) in ECL detection. In an embodiment, the S/BG ratio is improved by at least a factor of 1.2, in a further embodiment by at least a factor of 1.4. Moreover, it was found that the improving effect can be further enhanced by using Iridium labels. The accumulated effect of branched-chain tertiary amine and Iridium labels in a reagent composition leads to at least 1.3-fold improved S/BG ratio in ECL detection. Moreover, since the ECL reaction according to the present invention can be performed at a lower voltage, wearing in the working electrode is also reduced.

In an embodiment the present invention concerns a method for measuring an analyte in a sample via electrochemiluminescent detection, comprising the steps of a) incubating the sample with a detection reagent labeled with an electrochemiluminescent group, b) separating analyte-bound and analyte-free labeled detection reagent, c) incubating the separated labeled detection reagent with a reagent composition comprising i) at least one branched-chain tertiary amine as coreactant, and ii) Ru(bpy)$_3^{2+}$, d) electrochemically triggering the release of luminescence, and e) determining the electrochemiluminescence (ECL) signal thereby measuring the analyte.

In an embodiment, the methods of the present invention are characterized in that the reagent composition comprises in addition a detergent and/or a buffering agent.

In an embodiment, the methods of the present invention are characterized in that the reagent composition comprises in addition a salt and/or an anti-foam agent.

In an embodiment, the invention relates to a method for conducting an electrochemiluminescence assay wherein electrochemiluminescence is induced in the presence of a reagent composition according to the present invention.

A typical ECL measurement process for an ECL immunoassay comprises multiple exchanges of liquids and/or mixtures in the ECL measurement cell (e.g. a flow cell). In an embodiment, a typical ECL measurement process consists of several steps explained below.

The skilled artisan is aware that an ECL measurement cell, in an embodiment, is conditioned or regenerated before the ECL detection step takes place by rinsing said ECL measurement cell with a reagent composition according to the present invention and additional the application of an electric potential. This step, in an embodiment, is one part of the process of determining analytes using ECL. It has been described in EP 1 051 621 that during this conditioning step a layer is formed on the surface of the measurement electrode(s) supporting the signal generation during the measurement of an analyte in an ECL measurement cell.

In an embodiment of an ECL measurement process, a reagent mixture is introduced into the cleaned and conditioned ECL measurement cell through the fluid inlet channel into the ECL measurement cell cavity, wherein said mixture comprises constituents of the sample, reagents and magnetic particles. Said mixture introduced into the measurement cell may be surrounded by a reagent composition according to the present invention flowing in front and after said mixture.

In an embodiment, in such an ECL immunoassay a detection reagent comprising complex-molecules which are labeled with an electrochemiluminescent group and which are characteristic for the analysis, are bound to these magnetic particles by a pair of specific biochemical binding partners, e.g. streptavidin and biotin. The magnetic particles are for example coated with streptavidin-polymer, whereas biotin is bound to the complex-molecules.

In an embodiment, in the ECL measurement cell the magnetic particles are trapped to the surface of an electrode together with the labeled complex-molecules bound thereto in the magnetic field of a magnet arranged close to said electrode. The magnetic field is applied during a continuous flow of the mixture, whereby incubate and/or reagent composition discharges from the ECL measurement cell cavity through the fluid outlet channel.

After trapping the magnetic particles, a reagent composition according to the present invention containing an ECL coreactant is introduced into the ECL measurement cell in a next step, whereby the magnetic particles are washed by said reagent composition. This step of washing is to remove unbound components of said incubate from the electrode which potentially interfere with the electrochemical reaction. In an embodiment, the washing step may also be performed before contacting the magnetic particles with a reagent composition according to the present invention, e.g. with a washing buffer (pre-wash method).

Thereafter the release of the electrochemiluminescence (ECL) signal is electrochemically triggered by application of an electric potential, whereby the intensity of the luminescence light is detected by means of a photosensor and may be evaluated as a measure for the concentration of the labeled complex-molecules on the magnetic particles located at the surface of the electrode, whereby this concentration again serves as a measure for the concentration of the analyte in the sample.

After the electrochemiluminescence detection the ECL measurement cell usually is rinsed with a cleaning fluid.

An apparatus for carrying out detection methods by means of electrochemiluminescence is mentioned in the example section (Examples 2, 3, and 4) or described in EP 1 892 524 (A1). Moreover, such an apparatus can comprise means for controlling the temperature of the measuring unit and/or a liquid vessel. The measuring unit is understood to be a cell in which the electrochemiluminescence is measured. The liquid vessel can be a storage container, but also a feeding device; for example, a tube for the reagent solution, contained in the measuring unit during the measurement.

An aspect of the invention relates to improved reagent compositions for ECL-signal generation, in particular those which lead to enhanced signal to noise ratios (S/BG ratio). More specifically, the reagent compositions of the invention provide improved sensitivity at low detection levels by reducing the background electrochemiluminescence in the absence of ECL labels. Surprisingly a reagent composition comprising branched-chain tertiary amines emit less background luminescence than conventional test reagents without these compounds. This is particularly an advantage at low detection levels where increasing the signal to background ratio (=signal to noise ratio) greatly improves the sensitivity. This improved reagent composition contains a compound from the group of branched-chain tertiary amine as well as optional further ECL supporting reagents. Surprisingly the inventors have found that performing an electrochemiluminescent detection using a reagent composition according to the present invention results in a improved signal to noise ratio (S/BG ratio) of ECL detection as specified herein above.

An aspect of the invention relates to a reagent composition that gives high signal to background ratios in electrochemiluminescence assays. The signal difference between specific signals and background signals is increased. Such improved properties have been achieved through the identification of advantageous combinations of ECL coreactant, pH buffering agents, detergent and pH and, in particular, through the use of branched-chain tertiary amines as coreactands.

The reagent composition provides a suitable environment for efficiently inducing ECL labels to emit ECL and for sensitively measuring ECL labels via the measurement of ECL. The reagent composition of the invention may optionally comprise additional components including preservatives, detergents, anti-foaming agents, ECL active species, salts, acidic and basic compounds for pH control (buffering agents), metal ions and/or metal chelating agents. The reagent composition of the invention may also include components of a biological assay, which in some cases may be labeled with an ECL label, including binding reagents, enzymes, enzyme substrates, cofactors and/or enzyme inhibitors. The invention also includes assay reagents, compositions, kits, systems and system components that comprise the reagent composition of the invention and, optionally, additional assay components. The invention also includes methods for conducting ECL assays using the reagent composition of the invention.

In an embodiment the current invention relates to a reagent composition for detecting ECL, comprising
i) a branched-chain tertiary amine as coreactant, and
ii) optionally a further ECL reagent.

A definition and embodiments of the branched-chain tertiary amine are provided elsewhere herein. In an embodiment, the branched-chain tertiary amine of the reagent composition is selected from the group consisting of N,N-Dipropyl-N-(sec-butyl)amine (DPIBA, compound No: 25 of Table 1), N,N-Di(sec-butyl)-propylamine (DIBPA, compound No: 43 of Table 2), and N,N-Diisopropylethylamine (DIEA, CAS 7087-68-5, compound No: 32 of Table 2). In a further embodiment, the branched-chain tertiary amine is N,N-Dipropyl-N-(sec-butyl)amine or N,N-Di(sec-butyl)-propylamine. In a further embodiment, the branched-chain tertiary amine is N,N-Di(sec-butyl)-propylamine.

In an embodiment, the concentration of the branched-chain tertiary amine is selected optimally for the ECL enhancing effect, e.g. as shown in the Examples. Methods to determine the optimal concentration for a branched-chain tertiary amine in the reagent composition or reaction composition are known to the skilled artisan.

In an embodiment, the reagent composition comprises the branched-chain tertiary amine in a concentration of 50 mM to 500 mM. In a further embodiment the reagent composition comprises the branched-chain tertiary amine in a concentration of 75 mM to 350 mM. In a further embodiment, the reagent composition comprises the branched-chain tertiary amine in a concentration of 100 mM to 250 mM. It will be realized by the skilled person that, in case the reagent composition is provided as a stock solution, said stock solution may require dilution in order to obtain a reaction composition and that the concentration of constituents of such a stock solution may be adjusted according to the dilution factor intended. Thus, the aforesaid concentrations, in an embodiment, are final concentrations of the branched-chain tertiary amine in a reaction composition.

In an embodiment, the reagent composition of the present invention comprises a further ECL reagent. As used herein, the term "ECL reagent" includes ECL supporting reagents as well as ECL compounds comprising a transition metal complex, as specified elsewhere herein. ECL supporting reagents are, in principle, known to the skilled person. In an embodiment, an ECL supporting reagent is a preservative, a buffer compound, a detergent, an inorganic salt, in particular a sodium halogenide, or an anti-foaming agent, or any combination thereof. In an embodiment, the ECL supporting reagent is or comprises a carboxamide or amide. The term "carboxamide", in an embodiment, relates to a carboxamide described in WO 2012/055815 A1, in an embodiment relates to, optionally halogenated, acetamide, propanamide, or butyramide, in a further embodiment is propanamide.

It may be beneficial when storing a reagent composition to include a preservative that prevents microbial growth. Additionally, suitable preservatives are identified to control bacterial and fungal growth to enable long term storage and use of the reagent composition. The reagent composition according to the present invention may additionally contain one or more preservatives. In an embodiment of the present invention the reagent composition comprises a preservative (preservative agent) as specified elsewehere herein.

In an embodiment, the reagent composition further comprises a detergent. Suitable detergents for a reagent composition according to the present invention are those from the group consisting of fatty acid alcohol ethoxylates, including poly(ethylene glycol)ethers, for example polidocanol or other poly(ethylene glycol)ethers with the formula CxEOy with X=8-18 and Y=2-9, genapol (isotridecylpoly((ethylene glycol ether).), Plantaren® (alkylpolyglucoside), octylglucoside (octyl-beta-D-glucopyranoside) as well as zwitterionic detergents like Zwittergent 3-12 or a mixture thereof. The detergents are used in concentrations ranging between 0.01% and 2%. The optimal concentration can be easily determined for each detergent. The most suitable concentrations are those ranging between 0.05% and 1%. In an embodiment the reagent composition according to the present invention comprises detergents selected from the group consisting of polidocanol or other poly(ethylene glycol) ethers with the formula CxEOy with X=8-18 and Y=2-9, octylglucoside (octyl-beta-D-glucopyranoside) or zwitterionic detergents like Zwittergent 3-12 or a mixture thereof. In an embodiment the reagent composition comprises detergents selected from the group consisting of polydocanol, octylglucoside (octyl-beta-D-glucopyranoside) and Zwittergent 3-12, or a mixture thereof.

Further, in an embodiment the electrochemiluminescent signal can also be increased by adjusting the pH to a value between 6.0 and 8.0, in an embodiment between 6.0 and 7.5, in an embodiment between 6.2 and 6.9. This can be done conventionally by using a pH buffering agent suitable for this range, known to a person skilled in the art. In an embodiment the buffering agent suitable for the reagent composition comprises KOH and phosphoric acid ($H_3PO_4$); in an embodiment, the buffer is a sodium or potassium phosphate buffer, in an embodiment, a potassion phosphate buffer.

Furthermore, the signal can be increased by adding salts, including inorganic salts like, for example NaBr, NaCl, NaJ. The salts, especially NaCl, are added in concentrations ranging between 1 mM and 1 M, in an embodiment between 10 mM and 100 mM, in a further embodiment between 10 mM and 50 mM.

It may be beneficial, especially in HTS applications, to avoid the production of bubbles or foam. For this reason it may be desirable to add anti-foaming agents to a reagent composition. Many commercial antifoaming agents (including Antifoams o-30, Antifoam 204, Antifoam A, Antifoam SE-15, Antifoam SO-25 and Antifoam 289) may be added to the reagent composition according to the present invention.

The reagent composition of the invention may further include an ECL compound comprising a transition metal complex as specified elsewhere herein. The ECL compound comprising a transition metal complex may be a conventional ECL label. Examples of ECL labels include tris-bipyridyl-ruthenium (RuBpy) and other organometallic compounds where the metal is from, for example, the metals of group VII and VIII, including Re, Ru, Ir and Os. These ECL labels are used by a person skilled in the art to label an analyte specific reagent with an electrochemiluminescent group, or to label the analyte itself with an electrochemiluminescent group. In an embodiment the reagent composition of the invention contains an analyte labeled with an ECL compound comprising a transition metal complex and/or an analyte specific reagent labeled with an ECL compound comprising a transition metal complex as specified elsewhere herein.

The reagents and mixtures thereof used in the reagent composition may be provided either in liquid, frozen, deep frozen, vaporize frozen, lyophilized, gas, solid or dried form before usage. Before usage of the reagent composition, the reagents are, in an embodiment, dissolved in a solvent, in an embodiment in water.

The reagent compositions of the present invention are of particular value in high sensitivity assays. In some embodiments of the invention, the performance of ECL assays is improved even further through optimal combinations of reagent composition with electrode composition. In an embodiment, ECL electrodes for use in conjunction with the means and methods of the present invention comprise or consist of Au, Ir, Pt or Carbon, in an embodiment including boron-doped diamond electrodes.

For the determination of ECL, the reagent composition according to the present invention may be mixed with additional compounds forming a reaction composition. In an embodiment, the current invention relates to a reaction composition for determining ECL, comprising i) at least one ECL compound comprising a transition metal complex ii) at least one branched-chain tertiary amine as a coreactant. In an embodiment, the reaction composition further comprises an analyte.

In an embodiment, the present invention relates to an ECL reaction composition comprising i) at least one ECL compound comprising a transition metal complex, ii) at least one branched-chain tertiary amine as a coreactant, iii) an analyte, and iv) at least one analyte-specific reagent.

As will be appreciated by the skilled person, the at least one ECL compound comprising a transition metal complex and the at least one analyte-specific reagent may be covalently linked, i.e. may together be a detection reagent. It is, however, also envisaged that the ECL compound comprising a transition metal complex is bound to an agent specifically binding to the analyte-specific reagent. As will be appreciated by the skilled person, in an embodiment, the aforesaid reaction composition is a composition after removal of non-specifically bound ECL compound comprising a transition metal complex from the reaction mixture.

In a further embodiment, the reaction composition is a reaction composition for determining ECL, comprising i) at least one ECL compound comprising a transition metal complex covalently coupled to an analyte or to a structural analog of the analyte, ii) at least one branched-chain tertiary amine as a coreactant, and iii) an analyte.

In an embodiment, the aforesaid reaction compositions further comprise at least one further ECL supporting reagent as specified above.

An aspect of the present invention relates to the use of a branched-chain tertiary amine, of a reagent composition of the invention, or of a reaction composition of the invention, for performing an electrochemiluminescent detection method.

One aspect of the invention relates to kits comprising, in one or more containers, a branched-chain tertiary amine and an ECL reagent as specified herein above. The components may be optionally combined with additional reagents, to form the reagent composition or the reaction composition of the invention. The kits may also comprise in an embodiment additional assay related components such as a diluent, a washing solution, a protein denaturating reagent, one or more enzymes, a binding reagent, an assay plate, disposables, electrodes etc.

The term "kit", as used herein, refers to a collection of the aforementioned compounds, means or reagents of the present invention which may or may not be packaged together. The components of the kit may be comprised by separate vials (i.e. as a kit of separate parts) or provided in a single vial. Moreover, it is to be understood that the kit of the present invention is, in an embodiment, to be used for practicing the methods referred to herein above. It is, in an embodiment, envisaged that all components are provided in a ready-to-use manner for practicing the methods referred to above. Further, the kit, in an embodiment, contains instructions for carrying out said methods. The instructions can be provided by a user's manual in paper- or electronic form. In addition, the manual may comprise instructions for interpreting the results obtained when carrying out the aforementioned methods using the kit of the present invention.

In an embodiment, the chemical agents of the kit are contained in one or more glass or plastic containers, appropriately labeled with information regarding the contents and instructions regarding proper storage and use. Further information, which may relate to contents, lot number, production date, best before date, instructions regarding proper storage and use may be also stored on a RFID chip placed on the glass oder plastic containers. The information stored on such RFID chip can be read by an antenna connected to a RFID reader device and further processed in a control means.

In an embodiment some or all of the components of the reagent composition may be stored in an embodiment in a liquid or dry state.

In an embodiment the present invention concerns a kit for measuring ECL, which comprises a reagent composition for determining ECL as specified herein above.

The following examples and figures are provided to aid the understanding of the present invention, the true scope of which is set forth in the embodiments and claims. It is understood that modifications can be made in the procedures set forth without departing from the spirit of the invention.

A further aspect of the invention relates to an ECL device comprising a branched-chain tertiary amine as specified herein above.

The term "device", as used herein, relates to a system of means adapted for detecting ECL, further comprising at least the aforementioned means operatively linked to said device as to allow the result of the detection to be obtained. Typical means for operatively linking a branched-chain tertiary amine to the device of the present invention are containers linked to pumps, which, in an embodiment, mediate transfer of said branched-chain tertiary amine into a measuring chamber. How to link the means in an operating manner will depend on the type of means included into the device. In an embodiment, the means are comprised by a single device.

In an embodiment, the device comprises a sample treatment unit comprising a receptacle for a sample. The receptacle may directly contact the sample, or may be a receptacle for a further means receiving the sample, wherein the further means may be e.g. a multi-well plate, to which a sample or a multiplicity of samples may be applied. Moreover, the sample treatment unit, in an embodiment, comprises a branched-chain tertiary amine, e.g. in a dry form or in a reservoir connected to a dosing means, e.g. a tubing connected to a pump. In an embodiment, the sample treatment unit comprises at least one ECL compound comprising a transition metal complex, e.g. in a dried form or in a reservoir connected to a dosing means, e.g. a tubing connected to a pump. In a further embodiment, the sample treatment unit comprises means for mixing and means for adjusting the temperature of a reaction mixture. Optionally, the sample treatment unit may comprise a washing means for removing unspecifically bound ECL compound comprising a transition metal complex and/or binding agent.

In an embodiment, the result of the detection may be obtained in an analyzing unit of the device by visual inspection by the user or by performing a detection measurement on an appropriate device. In an embodiment, the analyzing unit of the device of the present invention further comprises a detection unit for detecting ECL according to the present invention. Means suitable as a detection unit according to the present invention are known to the skilled person and include, e.g. photometric devices, in particular luminometric devices.

In an embodiment, the device of the present invention further comprises a data output unit, connected to the detection unit. The data output unit, in an embodiment, is adapted to output data obtained by the detection unit. Suitable data output units are known to the skilled person and include simple output units such as an indicator lamp or a display indicating that ECL was detected above the detection threshold. An output unit may, however, also be an interface to an evaluation device, wherein said interface may be any kind of means of transferring data, including, e.g. cable connections like USB, wireless connections like wireless LAN, bluetooth, and the like, or indirect connections such as data transfer by instant messaging, email, or the like.

In an embodiment, the device of the present invention is part of an analytic system, said analytic system further comprising an evaluation device. As will be understood by the skilled person, the evaluation device may be comprised in the same housing as the device of the invention, e.g. as an evaluation unit, or may be a separate device. In an embodiment, the evaluation device comprises a microprocessor programmed to receive output data from an output unit of the device of the present invention and to perform logical operations providing an evaluation of said output data. Evaluation of output data may comprise, e.g., correcting data for values measured in one or more control detection reaction, statistical calculations, e.g. calculating means of two or more parallel detection reactions, correcting data for dilution factors, comparing output data to reference values, compiling data in a list, and the like. In an embodiment, the evaluation device further comprises a data storage unit. In a further embodiment, said data storage unit comprises reference values, e.g. in a reference value data base. Moreover, in an embodiment, the data storage unit is adapted to store output data received from a device of the present invention, as specified above.

In an embodiment, where means for automatically detecting ECL are applied, the data obtained by said automatically operating means can be processed by, e.g., a computer program in order to establish a diagnosis. Typical means for detection are disclosed in connection with embodiments relating to the methods of the invention above. In such a case, the means are operatively linked in that the user of the system brings together the result of the determination of ECL and the diagnostic value thereof due to the instructions and interpretations given in a manual. The person skilled in the art will realize how to link the means without further inventive skills. Typical devices are those which can be applied without the particular knowledge of a specialized clinician, e.g., test stripes or electronic devices which merely require loading with a sample. The results may be given as output of parametric diagnostic raw data, in an embodiment, as absolute or relative amounts. It is to be understood that these data will need interpretation by the clinician. However, also envisaged are expert system devices wherein the output comprises processed diagnostic raw data the interpretation of which does not require a specialized clinician.

In view of the above, the following embodiments are particularly envisaged:

1. A method of detecting an electrochemiluminescence (ECL) signal comprising
   a) contacting a reaction composition comprising
      i) at least one branched-chain tertiary amine and
      ii) an ECL compound comprising a transition metal complex with an electrode,
   b) electrochemically triggering the release of luminescence, and
   c) detecting the ECL signal.

2. The method of embodiment 1, wherein said branched-chain tertiary amine has the general structure of formula (I)

wherein
at least one of $R^1$, $R^2$, and $R^3$, in an embodiment one or two of $R^1$, $R^2$, and $R^3$ are independently selected side chains according to formula (II)

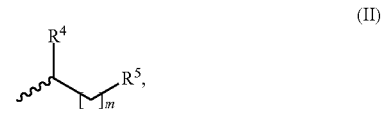

wherein
m is 0, 1, or 2, in an embodiment is 0 or 1;
$R^4$ is alkyl, in an embodiment is straight-chain $C_1$-$C_3$ alkyl, in a further embodiment is ethyl or methyl, in another embodiment is methyl,
$R^5$ is alkyl, in an embodiment is straight-chain C1-C3 alkyl, in another embodiment is ethyl or methyl, in an embodiment is methyl,
and wherein the residual groups $R^1$, $R^2$, and $R^3$ are independently selected from alkyl, in a further embodiment are independently selected from straight-chain alkyl, in another embodiment are independently selected from the group consisting of n-pentyl, n-butyl, n-propyl, ethyl and methyl, in an embodiment are independently selected from n-propyl, ethyl, and methyl.

3. The method of embodiment 1 or 2, wherein at least one of the residual groups $R^1$, $R^2$, and $R^3$ not being selected according to formula (II) is straight-chain alkyl, in an embodiment is selected from the group consisting of n-pentyl, n-butyl, n-propyl, ethyl or methyl, in a further embodiment is propyl, ethyl, or methyl.

4. The method of any one of embodiments 1 to 3, wherein said branched-chain tertiary amine is one of compounds 1 to 122 of any one of Tables 1 to 4.

5. The method of any one of embodiments 1 to 4, wherein said branched-chain tertiary amine is one of compounds 1 to 83 of any one of Tables 1 to 3.

6. The method of any one of embodiments 1 to 5, wherein said branched-chain tertiary amine is one of compounds 1 to 75 of Table 1 or 2.
7. The method of any one of embodiments 1 to 6, wherein said branched-chain tertiary amine is N,N-Dipropyl-N-(sec-butyl)amine (DPIBA), N,N-Di(sec-butyl)-N-propylamine (DIBPA), or N,N-Diisopropyl-N-ethylamine (DIEA), in an embodiment, is DPIBA or DIBPA, in a further embodiment is DPIBA, in a further embodiment is DIBPA.
8. The method of any one of embodiments 1 to 7, wherein said branched-chain tertiary amine is not triisopropylamine.
9. The method of any one of embodiments 1 to 8, wherein said electrode comprises or consists of Au, Ir, Pt or Carbon, in an embodiment is a boron-doped diamond electrode or a glassy carbon electrode; in an embodiment comprises or consist of platinum, gold, or glassy carbon, in an embodiment comprises or consists of platinum.
10. The method of any one of embodiments 1 to 9, wherein said electrochemically triggering the release of luminescence comprises applying a potential at the working electrode of from 0.8 V to 1.3 V, in an embodiment of from 0.9 V to 1.1 V versus an Ag/AgCl-electrode.
11. The method of any one of embodiments 1 to 10, wherein said transition metal complex comprises at least one of Ruthenium ions, Iridium ions, Rhenium ions, Osmium ions, Europium ions, Terbium ions, and Dysprosium ions; in an embodiment, wherein said transition metal complex comprises Ruthenium ions or comprises Iridium ions, in a further embodiment comprises Iridium ions.
12. The method of any one of embodiments 1 to 11, wherein said compound comprising a transition metal complex is selected from the list consisting of $Ru(bpy)_3^{2+}$, Ru(bpy)2-bpyCO-OSu), Sulfo-BPRu NHS Ester, BPRuUEEK-suberate-OSu, BPRu-(UE)-25-K-suberate-OSu, BPRu2-S K2-suberate-OSu, 4,4', 5,5-tetramethyl bipyridine Re(I)(4-ethyl pyridine)$(CO)_3^+CF_3SO_3^-$, Pt(2-(2-thienyl)pyridine)2, Ir(6-phenylphenanthridine)$_2$-2-(Carboxyethyl-phenyl)pyridine-2-carboxylic acid ester, and hydrophilic derivatives thereof.
13. The method of any one of embodiments 1 to 12, wherein said compound comprising a transition metal complex is selected from the list consisting of $Ru(bpy)_3^{2+}$, Ru(bpy)$_2$-bpyCO-OSu, Sulfo-BPRu NHS Ester, Ir(6-phenylphenanthridine)$_2$-2-(Carboxyethyl-phenyl)pyridine-2-carboxylic acid ester, or a hydrophilic derivative thereof, in an embodiment is Ir(6-phenylphenanthridine)$_2$-2-(Carboxyethyl-phenyl)pyridine-2-carboxylic acid ester.
14. The method of any one of embodiments 1 to 13, wherein said reaction composition comprises further ECL supporting reagents.
15. A method for detecting an analyte in a sample via electrochemiluminescence detection, comprising the steps of:
    a) incubating the sample with a detection reagent labeled with an electrochemiluminescent group comprising a transition metal complex, in an embodiment comprising a tris(2,2'-bipyridyl)ruthenium complex ($Ru(bpy)_3^{2+}$),
    b) separating analyte-bound and analyte-free labeled detection reagent,
    c) contacting the separated analyte-bound labeled detection reagent with a branched-chain tertiary amine as specified in any one of embodiments 1 to 8 and with an electrode,
    d) electrochemically triggering the release of luminescence, and
    e) detecting the electrochemiluminescence (ECL) signal thereby detecting the analyte.
16. A method for detecting an analyte in a sample via electrochemiluminescence detection, comprising the steps of:
    a) incubating the sample with a detection reagent labeled with an electrochemiluminescent group comprising a transition metal complex, in an embodiment comprising $Ru(bpy)_3^{2+}$,
    b) separating analyte-bound and analyte-free labeled detection reagent,
    c) detecting ECL according to the method of any one of embodiments 1 to 12, with the detection reagent being the compound comprising a transition metal complex, and
    d) detecting the analyte based on the result of the ECL detection in step c).
17. The method according to any one of embodiments 1 to 15, characterized in that the electrode comprises or consists of Au, Ir, Pt or Carbon, in an embodiment is a boron-doped diamond electrode or a glassy carbon electrode; in an embodiment comprises or consist of platinum, gold, or glassy carbon, in an embodiment comprises or consists of platinum.
18. The method according to any of embodiments 15 to 17, characterized in that detecting said analyte in a sample using ECL is performed in an aqueous solution.
19. The method according to any of embodiments 1 to 18, characterized in that the method is performed under homogeneous reaction conditions or heterogeneous reaction conditions, in an embodiment under homogeneous reaction conditions, in a further embodiment under heterogeneous reaction conditions.
20. The method according to any of embodiments 1 to 19, characterized in that the branched-chain tertiary amine is selected from the group consisting of N,N-Dipropyl-N-(sec-butyl)amine (DPIBA), N,N-Di(sec-butyl)-propylamine (DIBPA), and N,N-Diisopropyl-N-ethylamine (DIEA) in an embodiment is DPIBA or DIBPA.
21. The method according to any of the embodiments 1 to 20, characterized in that the reagent composition comprises a branched-chain tertiary amine in a concentration of at least 50 mM, in a concentration of at most 500 mM, in an embodiment in a concentration of 50 mM to 500 mM, in a further embodiment 75 mM to 350 mM, in a further embodiment 100 mM to 250 mM.
22. The method according to any of the embodiments 1 to 21, characterized in that the reagent mixture in the detection step comprises a preservative.
23. The method according to embodiment 22, characterized in that the reagent mixture in the detection step comprises said preservative in a concentration of 0.1% to 5%.
24. The method according to any of the embodiments 1 to 23, characterized in that the reagent mixture in the detection step comprises a detergent and a buffering agent.
25. The method according to any of embodiments 1 to 24, characterized in that the reagent mixture in the detection step further comprises a salt and/or an anti-foam agent, in an embodiment further comprises a carboxamide, in a further embodiment further comprises, optionally halogenated, acetamide, propanamide, or butyramide, in a further embodiment further comprises propanamide.

26. A reagent composition for detecting ECL, comprising
i) a branched-chain tertiary amine, in particular a branched-chain tertiary amine of Formula 1, as coreactant, and
ii) a further ECL reagent.

27. The reagent composition according to embodiment 26, wherein said further ECL reagent is an ECL compound comprising a transition metal complex, a preservative, a buffer compound, a detergent, an inorganic salt, in particular a sodium halogenide, an anti-foaming agent, or any combination thereof; and/or comprising a carboxamide, in a further embodiment, optionally halogenated, acetamide, propanamide, or butyramide, in a further embodiment propanamide.

28. The reagent composition according to embodiment 26 or 27, wherein, said further ECL reagent is an ECL compound comprising a transition metal complex.

29. The reagent composition according to any one of embodiments 26 to 28, wherein said further ECL reagent is an ECL compound comprising a iridium complex.

30. An ECL reaction composition comprising i) at least one ECL compound comprising a transition metal complex and ii) at least one branched-chain tertiary amine as a coreactant.

31. The ECL reaction composition of embodiment 30, further comprising an analyte.

32. The ECL reaction composition of embodiment 31, further comprising at least one analyte-specific reagent.

33. The ECL reaction composition of embodiment 32, wherein said analyte-specific reagent is covalently bound to said ECL compound comprising a transition metal complex.

34. The ECL reaction composition of embodiment 32, wherein said ECL compound comprising a transition metal complex is covalently bound to an agent specifically binding to said analyte-specific reagent.

35. The ECL reaction composition of embodiment 31, wherein said ECL compound comprising a transition metal complex is covalently bound to an analyte or to a structural analog of the analyte.

36. Use of a branched-chain tertiary amine as specified in any one of embodiments 1 to 8, of a reagent composition according to any one of embodiments 26 to 29, and/or of an ECL reaction composition according to any one of embodiments 30 to 35 in the detection of ECL.

37. A kit for detecting ECL comprising i) a branched-chain tertiary amine and ii) an ECL reagent.

38. The kit of embodiment 37, wherein said ECL reagent is an ECL compound comprising a transition metal complex and/or an ECL supporting reagent.

39. The kit of embodiment 37 or 38, further comprising an electrode, in an embodiment an electrode comprising or consisting of Au, Ir, Pt or Carbon, in an embodiment a boron-doped diamond electrode or a glassy carbon electrode; in a further embodiment an electrode comprising or consisting of platinum platinum, gold, or a glassy carbon electrode, in an embodiment embedded in a reaction chamber.

40. An ECL device comprising a branched-chain tertiary amine as specified in any one of embodiments 1 to 8.

Example 1

Synthesis/Sources of Compounds

N,N-Dipropyl-N-(sec-butyl)amine (CAS Registry Number 60021-91-2, "DPIB A") was synthesized according to Gheorghe, Ruxandra et al.; Chirality, 2008, Vol. 20, #10, p 1085-1091, and Takayama et al.; Journal of Organic Chemistry, 1979, Vol. 44, p2871-2872.

N,N-Di(sec-butyl)-propylamine (CAS Registry Number 1872850-05-9, DIBPA) was synthesized according the following procedure: 100 g di-sec-butylamine was dissolved in 420 ml methanol and cooled to 0° C. under vigorous stirring. 49.4 g propionaldehyde was dissolved in 82 ml methanol and slowly added to the solution. 205 g of sodium triacetoxyborohydride was added in 5 portions to the cooled solution the solution was stirred for 2 h at 0° C., afterwards slowly heated up to 30° C. and stirred at room temperature for 36 h. The suspension was filtrated and the solvent partly removed to ca. 500 ml by evaporation.

500 ml ethyl acetate and 500 ml $H_2O$ were added and the pH adjusted to pH 10 by adding a 10 molar NaOH solution. After separation of the organic phase the $H_2O$ phase was extracted another time with 500 ml ethyl acetate and the combined organic phases completely evaporated after drying.

The residue was distilled under high vacuum.

$^1$H-NMR (500 MHz): 0.85-0.99 ppm, 15 H (—$CH_3$), 1.21-1.43 ppm, 6 H (—$CH_2$—), 2.35-2.42 and 2.60-2.66 ppm, 4 H (—N—CH—).

Ethyl-diisopropyl-amine=diisopropylethylamine=CAS Registry Number 7087-68-5 (=DIEA) was from Sigma Aldrich.

Example 2

Voltage Dependence of Specific and Background Signals

ECL measurements were carried out using a Roche Elecsys® breadboard, which is similar to a Roche Elecsys® 1010 or a Roche Elecsys® 2010 comprising the capability to apply different potentials at the working electrode. The protocols for the assays mentioned below were used as recommended for Roche Elecsys® 2010. The dependence of ECL on measuring voltage was studied using buffers having various compositions. The general composition of the buffer was as follows:

300 mM Phosphate
0.1% polidocanol
coreactand as specified below; the final pH was adjusted to pH 6.8 using $KOH/H_3PO_4$. The coreactands and their concentrations were:
Buffer A (TPA): 180 mM tripropylamine
Buffer B (DPIBA): 120 mM dipropylisobutylamine
Buffer C (DIEA): 200 mM diisopropylethylamine
Buffer D (TBA): 180 mM tributylamine
Buffer E (EP): 200 mM ethylpiperidine
Buffer F (DIBPA): 80 mM diisobutylpropylamine The coreactand concentrations of the buffers reported here are the optimized concentrations with regard to signal yield. Buffer A comprises the buffer composition of ProCell without preservative and served as a reference buffer. ProCell is the state of the art buffer currently used for Elecsys analyzers. EP, TBA and Phosphate were purchased from Sigma Aldrich and were used without further purification.

Figure 2:
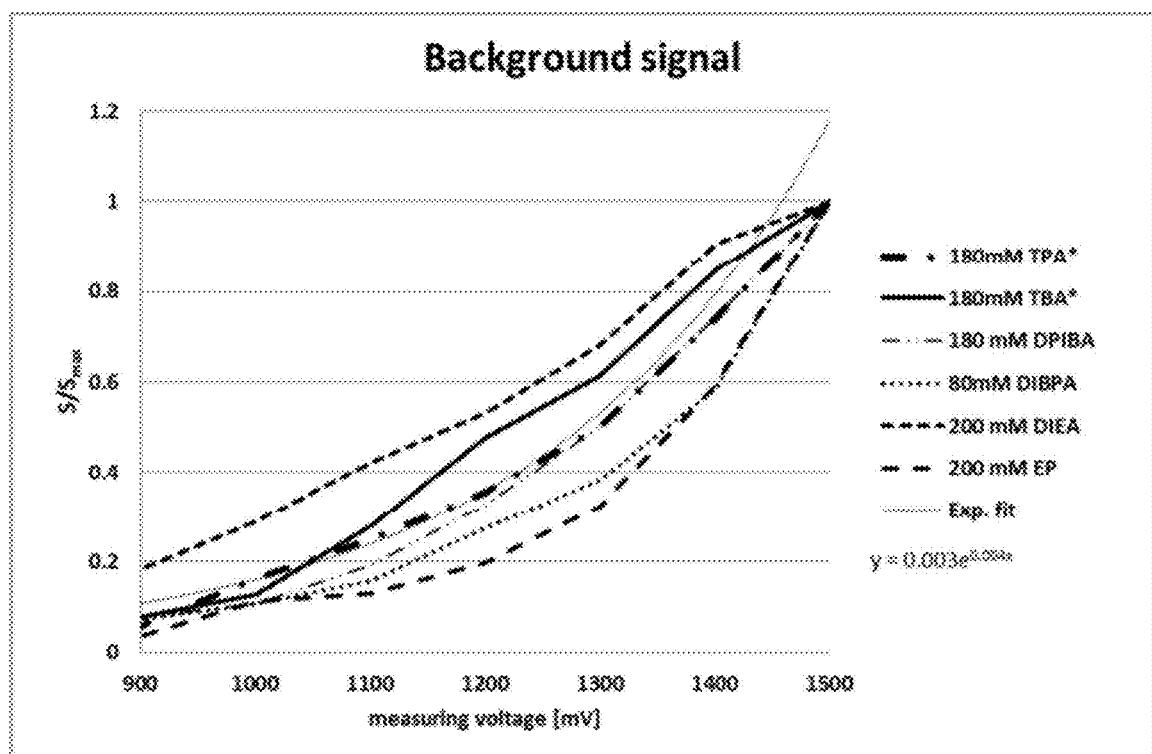
FIG. 2 shows the ECL signal measured in dependence on the applied measuring voltage in the absence of RuBpy labeled microparticles ("background signal") for 6 different coreactands. X-Axis: measuring voltage in mV, Y-Axis: signal intensity/maximal signal intensity (S/Smax); for further abbreviations cf. legend to FIG. 1.
Figure 3:
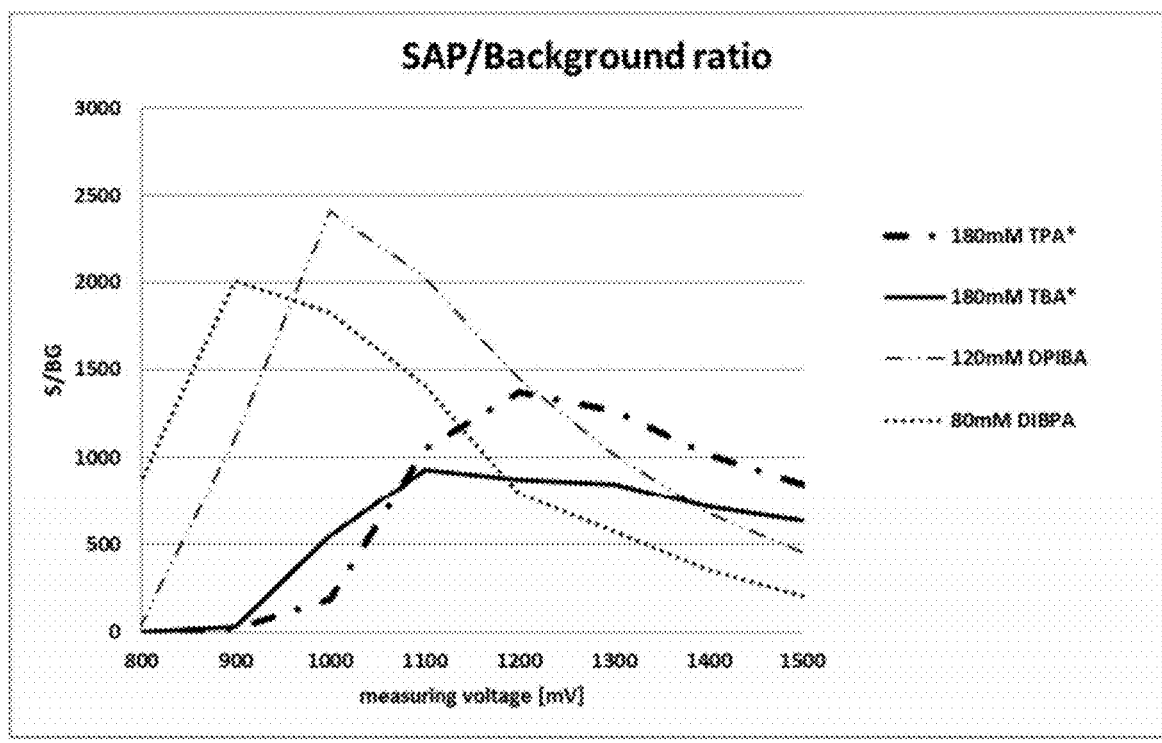
FIG. 3 shows the signal to background ratio (S/BG) in dependence on the applied measuring voltage for 4 different coreactands. X-Axis: measuring voltage in mV, Y-Axis: signal to background ratio.

Buffers A-F were used to determine the ECL of the assay buffer itself (background, FIG. 2) and of an artificial immunoassay (SAP, FIG. 1). The latter is an assay including RuBpy labeled microparticles for a high specific signal. Measurements of background and SAP where carried out at different measuring voltages and the ECL signal was recorded. The ratio between SAP and background is a good indicator to compare the impact of the different buffers on assay sensitivity (FIG. 3).

A consistent property of all amines is that their background increases exponentially with the applied voltage. A fair description for all curves is given by:

$$\frac{S}{S_{max}} = 0.003 \, e^{\frac{0.0039}{mV} U_{pot}} \quad \text{(Eq. 1)}$$

A commonly used measuring voltage for TPA is 1400 mV. According to Eq. 1, a voltage decrease to 1100 mV decreases the BG by a factor of ~3.8. However, this decrease is compensated by a strong loss in the specific ECL signal. In contrast, the unique voltage dependence of branched core-actands allows the utilization of low measuring voltages thus improving the S/BG ratio significantly.

Example 3

Assay Performance Comparison in TnT Assay

As a commercial in vitro diagnostic assay, the Elecsys® TnT assay (TroponinT1.Gen assay for Elecsys®; Order-No.: 05092744-190) was used to determine the signal to noise ratio. The analyte free sample (DilMa; Order-No.: 3609987) was used in the TnT assay to give the low level background signal (N). TnT calibrator 2 (TnT Cal 2; Order-No.: 05092752-190) was used in the TnT assay to give a high signal value (S).

Figure 4:
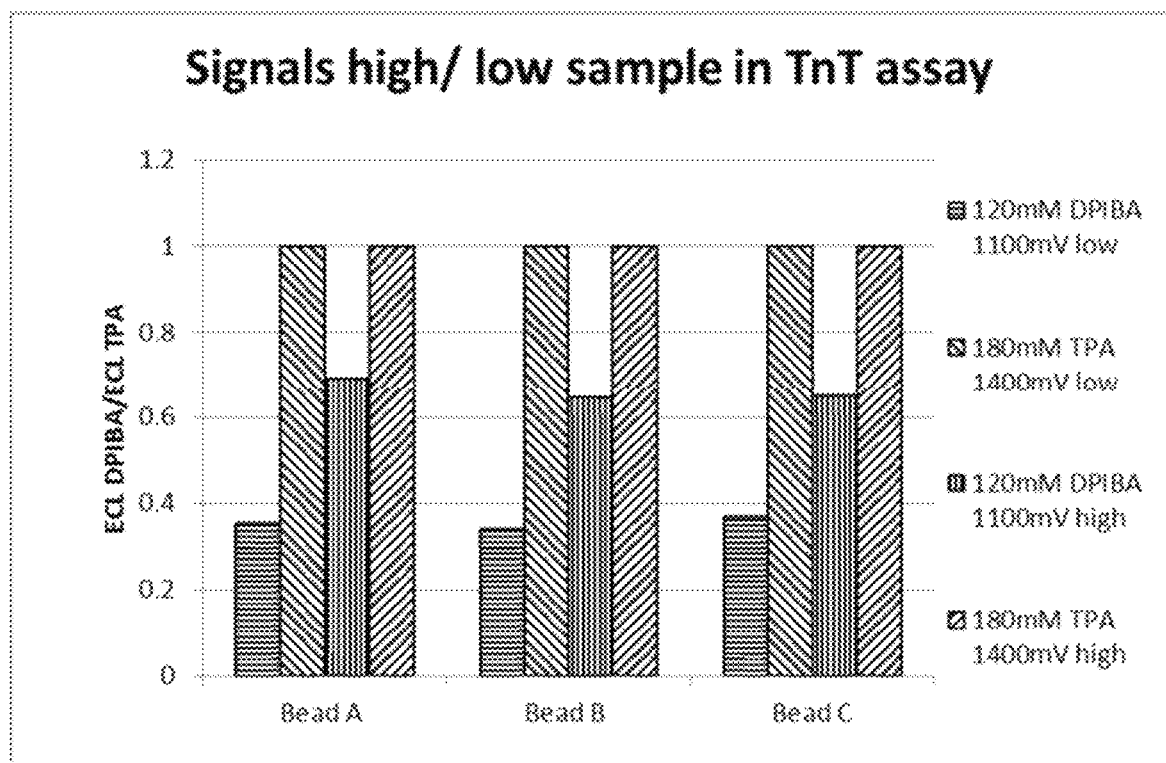
FIG. 4 comparison of background signal and positive control signals with various beads and two different coreactands in the SAP assay. Relative background ("low") and positive control signals ("high") for various bead types and buffers containing DBIPA or TPA. The signal obtained with TPA was set to 1. Apparently the usage of DPIBA leads to a decrease in background (low) and specific (high) signals. The decrease in the background signal however is stronger compared to the decrease in specific signal. This leads to an improved overall S/BG ratio.
Figure 5:
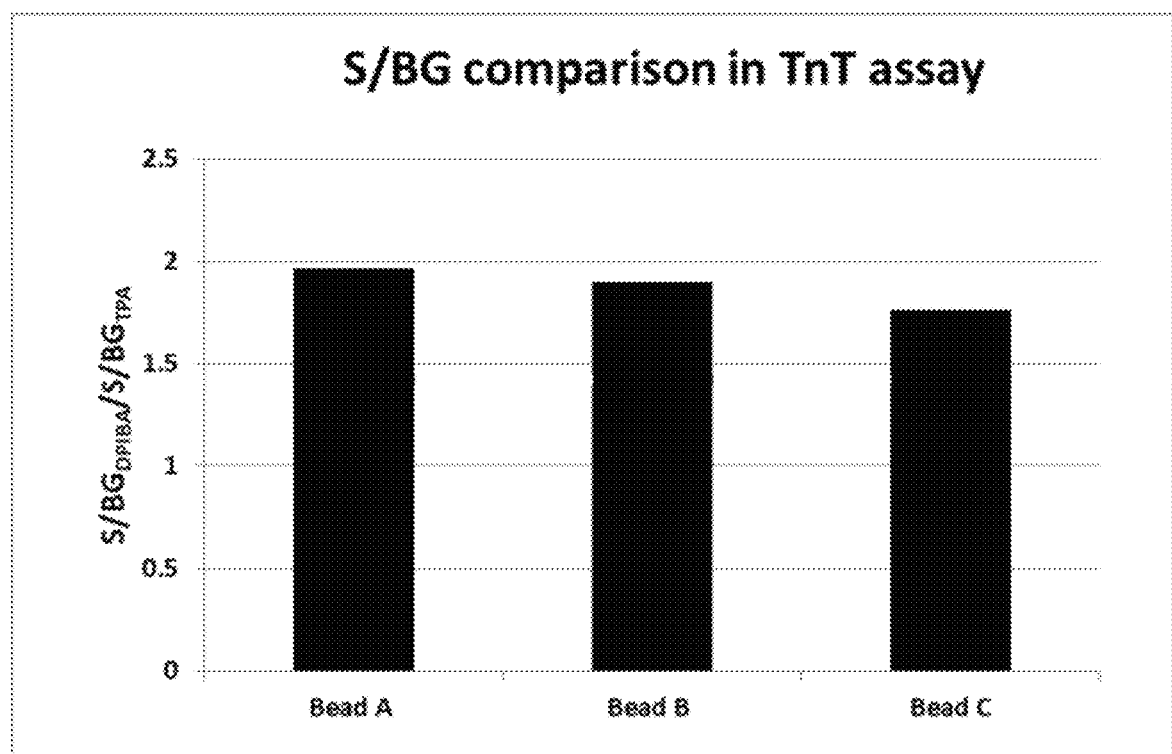
FIG. 5 improvement of S/BG ratio; S/BG ratio of samples measured in the presence of DPIBA relative to sample measured with TPA.
Figure 6:
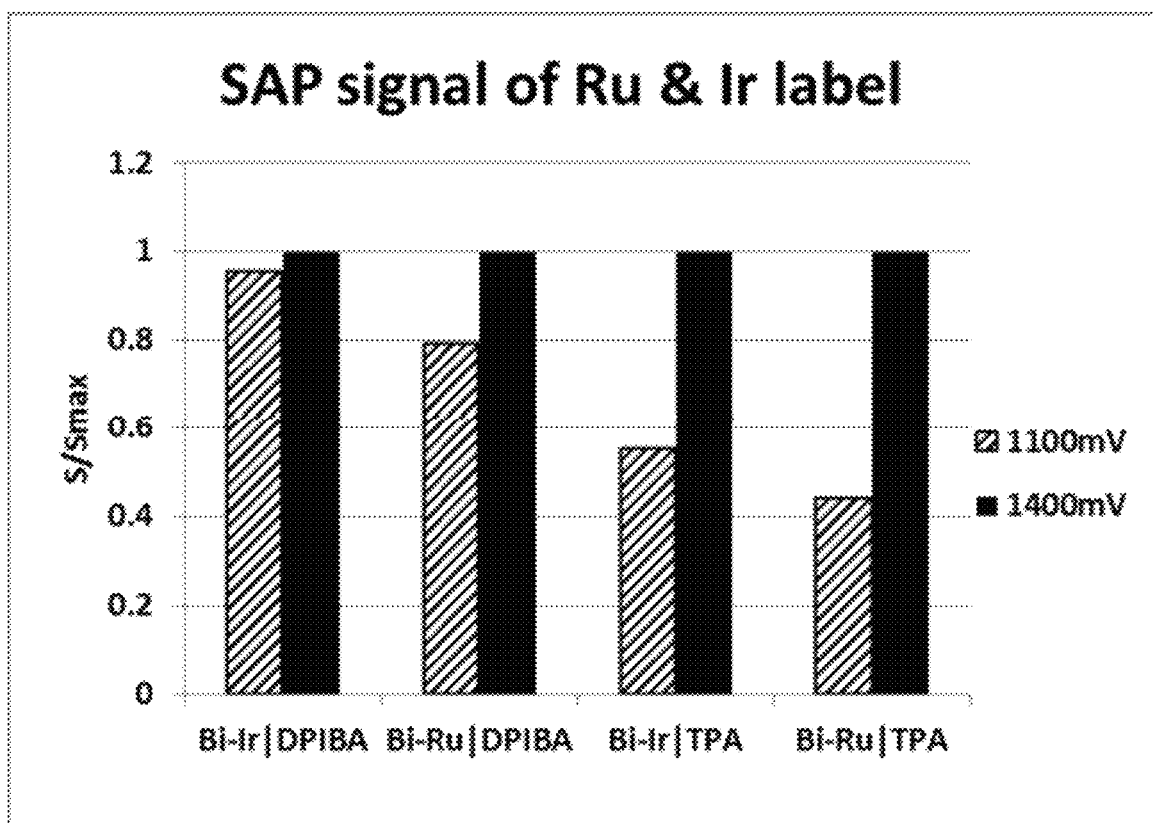
FIG. 6 comparison of Ru and Ir as transition metals in the method of the present invention in the SAP assay. If Ir label is used the decrease in the specific signal upon measuring at reduced voltage is lower compared to Ru label.
Figure 7:
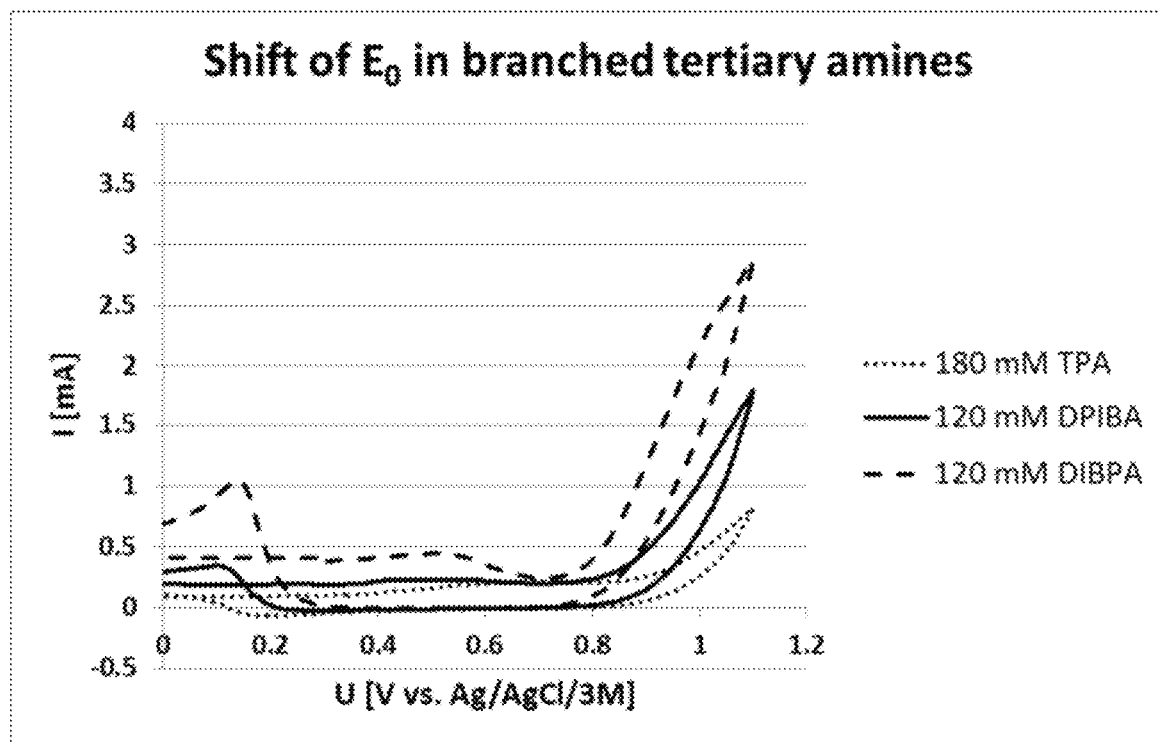
FIG. 7 shows the cyclic voltammetry data for 3 different coreactands. X-Axis: applied voltage in V, Y-Axis: current in mA; TPA: Tripropylamine, DPIBA: N,N-Dipropyl-N-(sec-butyl)amine, DIBPA N,N-Di(sec-butyl)-propylamine. With increasing number of branched substituents the oxidation current at a given potential increases due to a decrease of the standard oxidation potential of the compound.

Each assay was carried out using various bead types. These were bead A (standard Elecsys beads used in Elecsys® TnT assay), bead B (M-270, streptavidin coated carboxyl beads, Invitrogen) and Bead C (M-280, streptavidin coated tosyl beads, Invitrogen). To have a reference, the assays were carried out with buffer A under standard Elecsys conditions (1400 mV measuring voltage) using bead types A-C. The signals obtained served as a 100% reference for the standard conditions. A second set of experiments was carried in the same way but using buffer B and the optimized conditions according to the results found in example 2 (1100 mV measuring voltage) (FIG. 4). As can be seen from FIG. 5, an increase in S/BG ratio of ~2 can be achieved independently of the bead type used.

Example 4

Voltage Dependent Signal Behavior of Ir and Ru Label

Moreover, the voltage dependent signal behavior of Ruthenium and Iriduim labels in SAP assays was analyzed. In one case, the streptavidin coated microparticles used were labeled with Ruthenium-complexes (Biotin-DADOO-Sulfo-Ru, formula (VIII)) and in another case with Iridium-complexes (Biotin-DADOO-IB3/47, formula (IX)). Signals were normalized with the maximum ECL signal to compare the curves. In case of Ir-label, 6% of the specific signal is lost when the measuring voltage is lowered from 1400 mV to 1100 mV. The same decrease in measuring voltage leads to a 28% signal decrease in the case of Ru-label.

Biotin-DADOO-Sulfo-BPRu:

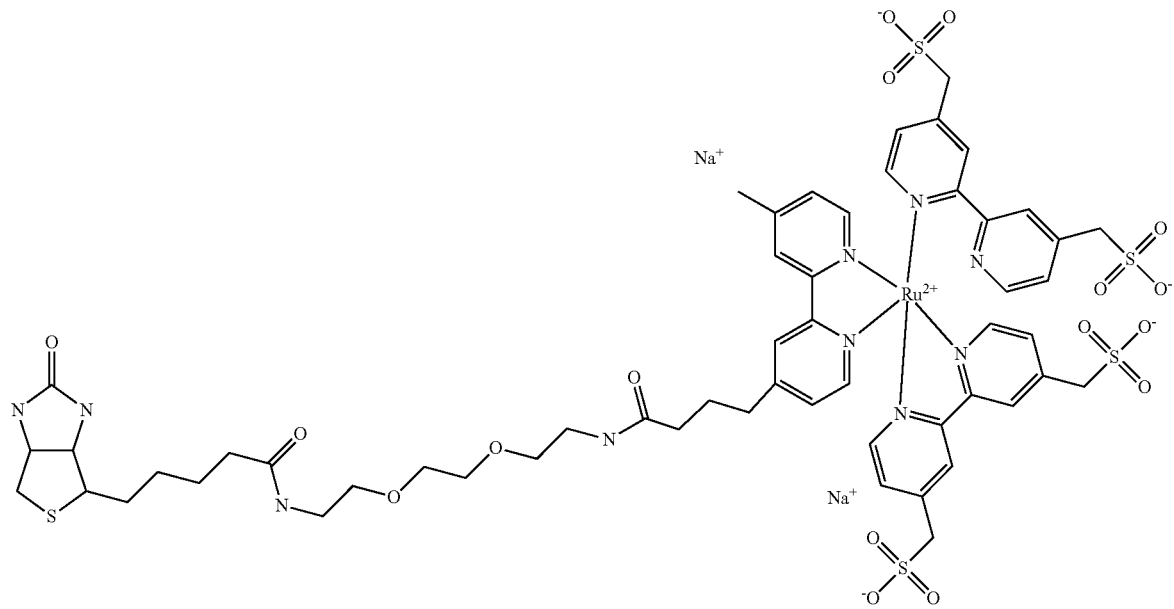

formula (VIII)

Biotin-DADOO-IB3/47:

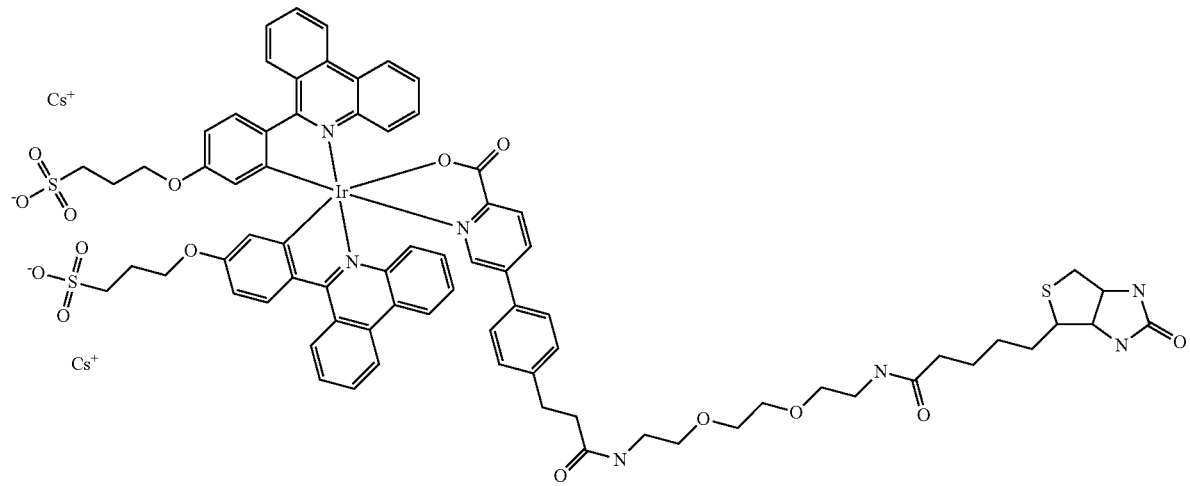

formula (IX)

Example 5

Impact of Alpha-Branched Side Chains on Amine Oxidation Potential

In order to evaluate the effect of side chain branching on tertiary amine oxidation potentials, cyclic voltammograms (CVs) of TPA, DPIBA and DIBPA in phosphate buffer were recorded. The coreactand solutions were introduced into an Elecsys measuring cell V 7.0 which was connected to a SP-300 Potentiostat from Biologic, France. The open circuit potential was chosen as a starting potential and the CV was measured at a scanrate of 0.3 V/s between 1.1 and −0.5 V. The obtained CVs were subsequently fitted with the fit function available in the potentiostat software (EC-labs) to estimate the standard oxidation potential of the different coreactands. Obviously the oxidation potential is reduced from TPA to DPIBA to DIBPA in line with the number of branched side chains of the different coreactands. The reduced oxidation potential of such amines explains the reduced potential necessary for ECL generation.

The invention claimed is:

1. A method of detecting an electrochemiluminescence (ECL) signal comprising
   a) contacting a reaction composition comprising
      i) at least one branched-chain tertiary amine and
      ii) an ECL compound comprising a transition metal complex with an electrode,
   b) electrochemically triggering the release of luminescence, and
   c) detecting the ECL signal,
wherein said branched-chain tertiary amine is one of compounds 1 to 122 of any one of Tables 1 to 4.

2. The method of claim 1, wherein said branched-chain tertiary amine is one of compounds 1 to 83 of any one of Tables 1 to 3.

3. The method of claim 1, wherein said branched-chain tertiary amine is one of compounds 1 to 75 of Table 1 or 2.

4. The method of claim 1, wherein the branched-chain tertiary amine is a compound according to the general formula (VII):

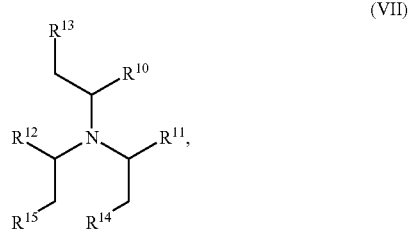

wherein $R^{10}$ to $R^{15}$ are independently selected from —H and methyl, wherein at least one of $R^{10}$ to $R^{12}$ is methyl; and wherein if $R^{10}$, $R^{11}$ and $R^{12}$ are methyl, at least one of $R^{13}$ to $R^{15}$ is methyl.

5. The method of claim 1, wherein said branched-chain tertiary amine is N,N-Di(sec-butyl)-propylamine ("N,N-Di-isobutyl-propylamine", DIBPA), N,N-Dipropyl-N-(sec-butyl)amine ("N,N-Dipropyl-isobutylamine", DPIBA), and/or N,N-Diisopropyl-N-ethylamine (DIEA).

6. The method of claim 1, wherein said branched-chain tertiary amine is DIBPA or DPIBA, in an embodiment is DIBPA, in an embodiment is DPIBA.

7. The method of claim 1, wherein said transition metal complex comprises at least one of an Iridium ion, a Ruthenium ion, a Rhenium ion, an Osmium ion, a Europium ion, a Terbium ion, and a Dysprosium ions.

8. The method of claim 1, wherein said transition metal complex comprises a Ruthenium ion or comprises an Iridium ion.

9. The method of claim 1, wherein said compound comprising a transition metal complex is selected from the list consisting of Ru(bpy)$_3^{2+}$, Ru(bpy)2-bpyCO-OSu), Sulfo-BPRu NHS Ester, BPRuUEEK-suberate-OSu, BPRu-(UE)-25-K-suberate-OSu, BPRu2-SK2-suberate-OSu, 4,4',5',5-tetramethyl bipyridine Re(I)(4-ethyl pyridine)(CO)$_3^+$ CF$_3$SO$_3^-$, or Pt(2-(2-thienyl)pyridine)2, Ir(6-phenylphenanthridine)$_2$-2-(Carboxyethyl-phenyl)pyridine-2-carboxylic acid ester, and hydrophilic derivatives thereof.

10. The method of claim 1, wherein said electrode comprises or consists of Au, Ir, Pt or Carbon.

11. The method of claim 1, wherein said electrode is a boron-doped diamond electrode or a glassy carbon electrode.

12. The method of claim 1, wherein said electrode comprises or consists of platinum, gold, or glassy carbon, in an embodiment comprises or consists of platinum.

13. The method claim 1, wherein said electrochemically triggering the release of luminescence comprises applying a potential at the working electrode of from 0.8 V to 1.3 V, in an embodiment of from 0.9 V to 1.1 V versus an Ag/AgCl-electrode.

14. The method according to claim 1, characterized in that the reagent composition comprises a branched-chain tertiary amine in a concentration of 50 mM to 500 mM.

15. A method for detecting an analyte in a sample via electrochemiluminescence detection, comprising the steps of:
  a) incubating said sample with a detection reagent labeled with an electrochemiluminescent group comprising a transition metal complex, in an embodiment comprising tris(2,2'-bipyridyl)ruthenium complex $(Ru(bpy)_3^{2+})$,
  b) separating analyte-bound and analyte-free labeled detection reagent,
  c) detecting ECL according to the method of claim 1, with said detection reagent being said compound comprising a transition metal complex, and
  d) detecting the analyte based on the result of the ECL detection in step c).

* * * * *